United States Patent
Wach et al.

(10) Patent No.: US 9,795,763 B2
(45) Date of Patent: Oct. 24, 2017

(54) DELIVERY DEVICES, SYSTEMS AND METHODS FOR DELIVERING THERAPEUTIC AGENTS

(71) Applicants: EMORY UNIVERSITY, Atlanta, GA (US); CELL PRECISION, LLC, Atlanta, GA (US)

(72) Inventors: Michael L. Wach, Alpharetta, GA (US); Raymond P. Vito, Atlanta, GA (US); Jack Griffis, Decatur, GA (US); W. Robert Taylor, Stone Mountain, GA (US)

(73) Assignee: CELL PRECISION, LLC, Smyrna, GA (US)

( * ) Notice: Subject to any disclaimer, the term of this patent is extended or adjusted under 35 U.S.C. 154(b) by 359 days.

(21) Appl. No.: 14/427,031

(22) PCT Filed: Sep. 4, 2013

(86) PCT No.: PCT/US2013/057921
§ 371 (c)(1),
(2) Date: Mar. 10, 2015

(87) PCT Pub. No.: WO2014/039471
PCT Pub. Date: Mar. 13, 2014

(65) Prior Publication Data
US 2015/0238728 A1    Aug. 27, 2015

Related U.S. Application Data

(60) Provisional application No. 61/698,884, filed on Sep. 10, 2012.

(51) Int. Cl.
*A61M 5/178* (2006.01)
*A61M 25/00* (2006.01)
(Continued)

(52) U.S. Cl.
CPC ..... *A61M 25/0084* (2013.01); *A61B 17/3205* (2013.01); *A61M 5/3204* (2013.01);
(Continued)

(58) Field of Classification Search
CPC .. A61M 2025/0087; A61M 2025/0089; A61M 2025/0096; A61M 25/0082;
(Continued)

(56) References Cited

U.S. PATENT DOCUMENTS 5,362,251 A * 11/1994 Bielak ............... H01R 9/053
439/394
6,692,504 B2 * 2/2004 Kurz ............... A61B 17/22031
604/106

(Continued)

OTHER PUBLICATIONS

International Preliminary Report on Patentability for PCT/US2013/057921; dated Mar. 10, 2015; 8 pgs.

(Continued)

*Primary Examiner* — Rebecca E Eisenberg
(74) *Attorney, Agent, or Firm* — Gardner Groff Greenwald & Villanueva, PC

(57) ABSTRACT

Delivery devices, systems, and methods are configured to enhance retention of a therapeutic agent delivered at a treatment site, for example, via impeding agent backflow. A device may include sheath having a first end, a second end, and a length between the first end and the second end. The sheath may include an outer diameter and an inner channel between the first end and the second end, and at least one penetrating member configured to form a channel at the treatment site. The device may include an elongate member having a first end, a second end, and a length between the first end and the second end, the elongate member being configured to move relative to the sheath. The elongate member may be configured to control the movement of the penetrating member with respect to the sheath.

19 Claims, 15 Drawing Sheets

(51) Int. Cl.
*A61B 17/3205* (2006.01)
*A61M 5/32* (2006.01)

(52) U.S. Cl.
CPC . *A61M 25/0082* (2013.01); *A61M 2025/0087* (2013.01); *A61M 2025/0089* (2013.01); *A61M 2025/0096* (2013.01); *A61M 2210/125* (2013.01)

(58) Field of Classification Search
CPC ............ A61M 25/0084; A61M 5/3204; A61M 2025/0057; A61M 25/007; A61B 17/320725
See application file for complete search history.

(56) References Cited

U.S. PATENT DOCUMENTS

| | | | |
|---|---|---|---|
| 7,331,947 B2 | 2/2008 | McGuckin, Jr. et al. | |
| 7,850,644 B2 | 12/2010 | Gonzalez et al. | |
| 8,075,519 B2 | 12/2011 | Min et al. | |
| 2005/0124977 A1* | 6/2005 | Gonzalez | A61B 17/3478 604/534 |
| 2005/0273049 A1 | 12/2005 | Krulevitch et al. | |
| 2010/0168656 A1 | 7/2010 | Lee et al. | |

OTHER PUBLICATIONS

International Search Report for PCT/US2013/057921; dated Dec. 2, 2013; 3 pgs.

\* cited by examiner

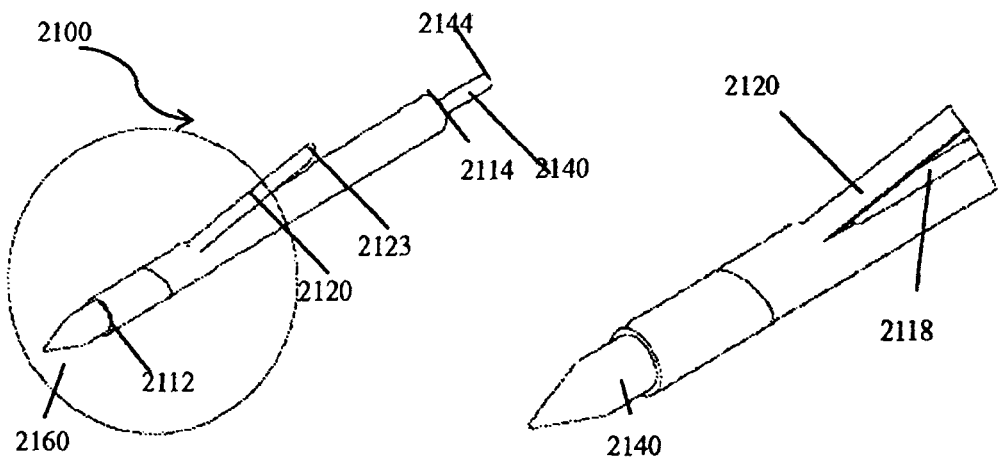
FIGURE 27
FIGURE 28
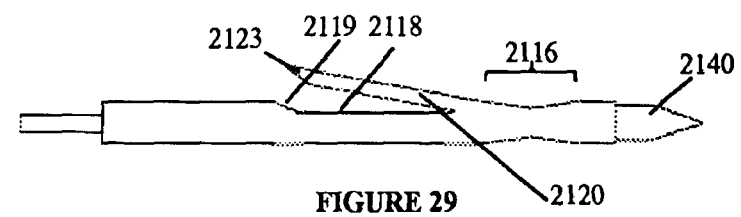
FIGURE 29
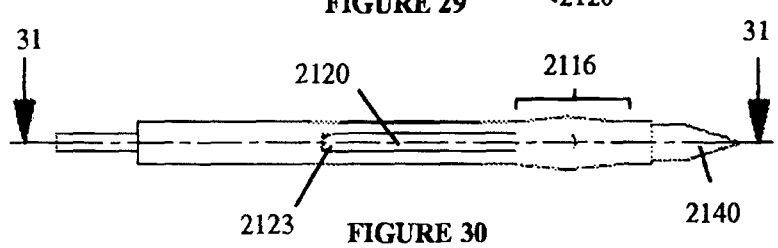
FIGURE 30
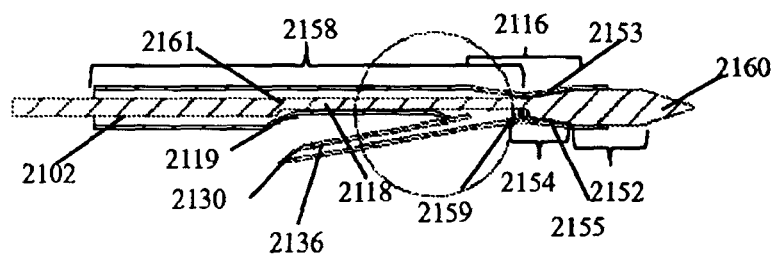
FIGURE 31
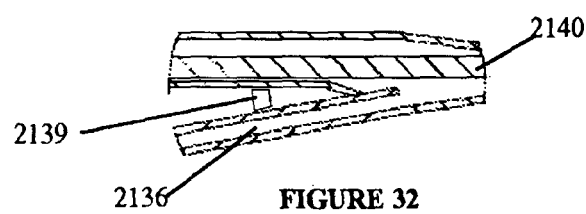
FIGURE 32

DELIVERY DEVICES, SYSTEMS AND METHODS FOR DELIVERING THERAPEUTIC AGENTS

CROSS REFERENCE TO RELATED APPLICATION

This application claims priority to Provisional Application Ser. No. 61/698,884 filed Sep. 10, 2012, which is hereby incorporated by reference in its entirety.

BACKGROUND

An emerging approach to treating disease entails delivering a therapeutic agent at the treatment site and focuses the therapeutic agent's effect on the diseased tissue.

Conventional technologies for delivering such agents generally lack sufficient sophistication for realizing full therapeutic potential. Aggressive handling resulting from these technologies, such as attempting to inject the agents with a conventional syringe, may compromise therapeutic effectiveness due to shear forces, imprecise placement at a treatment site, and leakage or escape of the agents from the treatment site after the delivery. For example, retaining therapeutic cells, such as stem or progenitor cells, injected into the myocardium can be challenging with conventional technologies, as forces of the beating heart may tend to eject the cells from the treatment site prior to realizing therapeutic potential.

Accordingly, a need exists for improved delivery methods and devices.

SUMMARY

The disclosure relates to delivery devices, systems, and methods for delivering a therapeutic agent. These devices, systems, and methods may reduce or eliminate leakage associated with the delivery of an agent, as the structure of the delivery device is configured to block or curtail backflow of the therapeutic agent along the path used to deliver the agent to the treatment site, for example in connection with increasing or sustaining pressure at the treatment site.

In some embodiments, the disclosure relates to a delivery device for delivering an agent to a treatment site. In some embodiments, the delivery device may include a sheath having a first end, a second end, and a length between the first end and the second end. The sheath may include an outer diameter and an inner channel between the first end and the second end, including at least one penetrating member configured to form a channel at the treatment site. The sheath may include at least one penetrating member, the penetrating member being configured to be movable between a first position and a second position, the first position corresponding to when the penetrating member is substantially aligned with the outer diameter, and the second position corresponding to when the penetrating member protrudes from the outer diameter at an angle towards one of the first end and the second end.

In some embodiments, the delivery device may further include an elongate member having a first end, a second end, and a length between the first end and the second end, the elongate member being configured to move relative to the sheath. The elongate member may be configured to control the movement of the penetrating member with respect to the sheath. In some embodiments, the device may be configured to deliver the agent when the penetrating member is in the second position.

In some embodiments, the penetrating member may be configured to form a channel at the treatment site. The penetrating member may be configured to form a channel by at least one of cutting the tissue, partially coring or entirely coring tissue at the treatment site. The channel may include at least one of a delivery channel and/or a pressure channel. The channel may include at least one delivery channel into which an agent may delivered by the delivery device and/or at least one pressure channel configured to generate pressure at the treatment site.

In some embodiments, the elongate member may include a plurality of diameters, the diameters being configured to control the movement of the penetrating member.

In some embodiments, the sheath may include a depressible section, the depressible section being configured to move between an aligned position and a depressed position, the aligned position corresponding to when the depressible section is substantially aligned with the outer diameter and the depressed position including when the depressible section is depressed into the inner channel of the sheath. The penetrating member and the depressible section may be configured so that the position of the penetrating member depends on the position of the depressible section; and the elongate member may be configured to control the movement of the depressible section. In some embodiments, the elongate member may include at least one tapered surface configured to cause the depressible section to move to the depressed position when adjacent to a portion of the depressible section.

In some embodiments, the sheath may include at least one opening configured to deliver the agent to the treatment site. In some embodiments, the opening may be disposed at one of the ends of the sheath. In other embodiments, the opening may be disposed adjacent to the depressible section.

In some embodiments, the sheath may include two opposing penetrating members. In some embodiments, the sheath may include two opposing openings, each of the penetrating members being configured to be disposed within one of the openings when in the first position, and the penetrating members may be configured to expose each of the openings when in the second position. In some embodiments, the delivery device may be configured to deliver the agent through the openings when the penetrating members are in the second position.

In some embodiments, the penetrating member may have a length and an inner channel that extends along the length. The opening may be disposed at one end of the channel. The delivery device may be configured to deliver the agent through the opening when the penetrating member is in the second position.

In some embodiments, a device for delivering an agent to a treatment site may include a sheath having a first end, a second end, and a length between the first end and the second end, the sheath having an outer diameter, the sheath including a section that is configured to reversibly depress from the outer diameter. In some embodiments, the sheath may include at least one penetrating member configured to be movable between an aligned position and a protruded position with respect to the length disposed at the section. In some embodiments, the device may include an elongate member having a first end, a second end, and a length between the first end and the second end, the elongate member being configured to move relative to the sheath. The aligned position may correspond to when the penetrating member is parallel with the outer diameter and the protruded position may correspond to when the penetrating member protrudes from the outer diameter into the treatment site.

In some embodiments, the penetrating member may include a puncture member. In some embodiments, the penetrating member may include a puncture tip. In some embodiments, the penetrating member may include at least one puncture edge. In some embodiments, the penetrating member may include two puncture edges.

In some embodiments, the elongate member may include a plurality of sections, at least one of the sections of the elongate member being configured to control the position of at least the penetrating member based on position of the elongate member with respect to the sheath. In some embodiments, the section of the sheath may be configured to be depressed when one of the sections is adjacent to a portion of the section of the sheath. The penetrating member may be configured to protrude from the outer diameter when the section of the sheath is depressed from the outer diameter.

In some embodiments, the elongate member may include a puncture member. In some embodiments, the puncture member may be disposed at one end of the elongate member. In some embodiments, the puncture member may be a puncture tip. In some embodiments, the elongate member may be solid.

In some embodiments, the elongate member may include at least one groove partially along its length. In some embodiments, the groove may be configured to allow flow of the agent through an inner channel of the sheath. In some embodiments, the elongate member may include four grooves disposed evenly around a circumference of the elongate member.

In some embodiments, the elongate member may include at least a first section, a second section, and a third section, the sections having different diameters. In some embodiments, the second section may include at least one tapered surface. In some embodiments, the second section may include a tapered surface on each side. In some embodiments, the tapered surfaces may be symmetric. In other embodiments, the tapered surfaces may be asymmetric. In other embodiments, the second section may include a tapered surface on one side.

In some embodiments, the sheath may include an opening that corresponds to each penetrating member. The penetrating member may be configured to be disposed within the opening when in the aligned position. The penetrating member may be configured to expose the opening when in the protruded position.

In some embodiments, the elongate member may be configured to control a size of the opening. In some embodiments, the elongate member may include a tapered surface on at least one side of the elongate member, the side facing the penetrating member.

In some embodiments, the sheath may include two opposing penetrating members and openings. In some embodiments, the penetrating members may be of the same size. In some embodiments, the openings may be of the same size when the corresponding penetrating member is in the protruded position. In other embodiments, the openings may be of different sizes when the corresponding penetrating member is in the protruded position.

In some embodiments, the penetrating member may have an elongated shape and a length, and a channel along the length. In some embodiments, the penetrating member may include an opening disposed at an end of the channel. In some embodiments, the channel of the penetrating member may be in fluid communication with the inner channel of the sheath.

In some embodiments, the elongate member may include a track configured to control the movement of the elongate member with respect to the sheath. In some embodiments, the track may include tapered edge that is configured to restrain the movement of the elongate member with respect to the sheath.

In some embodiments, the sheath may include an indented section. In some embodiments, the indented section may be disposed adjacent to the depressible section. In some embodiments, the length indented section may substantially correspond to the length of the track. In some embodiments, the penetrating member may be configured to extend within the indented section when in the aligned position. The indented section may include a surface that is configured to substantially seal the opening of the penetrating member when in the aligned position.

In some embodiments, a catheter for delivering stem cells may include: a distal section that extends longitudinally; one or more lumens, extending through the distal section, operable to convey the stem cells for delivery in tissue; and a member that is attached to the distal section, that moves laterally open and closed, that includes at least one sharp surface or edge configured to penetrate tissue, and that is operable to form a valve in the tissue for retention of stem cells delivered via the one or more lumens.

In further embodiments, the disclosure relates to a method of delivering a therapeutic agent. In some embodiments, the method may include positioning a delivery device at a treatment site, the delivery device including a sheath including a penetrating member and an elongate member that is configured to move with respect to the sheath; moving the elongate member with respect to the sheath toward the treatment site; causing the penetrating member to protrude into the treatment site; and delivering the therapeutic agent.

In some embodiments, the method may include creating in tissue a channel that includes a kink or makes an abrupt turn; and delivering the therapeutic agent into the channel beyond the kink or abrupt turn. In some embodiments the channel may turn back on itself, for example extending to a tissue depth and then cutting back in an acute angle. In longitudinal cross section, a path of such a channel may resemble a "check mark." When the therapeutic agent is delivered through the channel past the kink or abrupt turn, the resulting delivery pressure may pinch the portion of the channel that leads to the kink, thereby closing the channel and producing pressure and retaining the agent in the portion of the channel that is past the kink. In some embodiments, a device for delivering an agent to a treatment site may by adapted to perform such a method.

In some embodiments, the method may include mechanically creating in tissue a channel that extends from a proximal entry location to a distal depth and that includes a branch located between the proximal entry location and the distal depth. The branch may extend proximally, for example such that an acute angle is formed between the branch and a section of the channel that is between the branch and the proximal entry location. Delivering a therapeutic agent into the branch may pinch the section of the channel that is between the branch and the proximal entry location, thereby retaining the therapeutic agent within the branch. In some embodiments, a device for delivering an agent to a treatment site may by adapted to perform such a method.

In some embodiments, the method may include creating a channel that extends in tissue from a proximal entry site to a distal depth and making in the tissue a generally conical cut that circumscribes the channel at a location between the proximal entry site and the distal depth. The cut may form a structure in the tissue that closes the channel when the therapeutic agent is delivered through the channel to the distal depth. The tissue structure may have a form generally resembling a conical solid (with the channel itself extending through the conical solid). The tissue structure may function like a check valve, allowing transport of the therapeutic agent in the distal direction but impeding flow in the reverse, proximal direction. When the therapeutic agent is injected to a distal location relative to the tissue structure, the tissue structure may close the channel, to create a pressurized environment and retain the agent. In some embodiments, a device for delivering an agent to a treatment site may by adapted to perform such a method.

In some embodiments, the method may include creating in the myocardium a cell delivery channel and an accompanying check valve; delivering cells into the channel; and retaining the cells in the channel via the check valve. In some embodiments, a device for delivering an agent to a treatment site may by adapted to perform such a method.

In some embodiments, the method may include: forming in myocardial tissue a channel that includes: a first section extending distally into the myocardial tissue and a second section joined with the first section and extending proximally in the myocardial tissue; and delivering a fluid comprising therapeutic cells into the second section, whereby the delivered fluid pinches the first section of the channel to retain the therapeutic cells. In some embodiments, a device for delivering an agent to a treatment site may by adapted to perform such a method.

In some embodiments, the method may include creating in myocardial tissue a tapered structure with a channel extending through the tapered structure; and injecting therapeutic cells in the channel beyond the tapered structure, wherein the tapered structure and the injected therapeutic cells cooperatively close the channel to impede or reduce backflow of the therapeutic cells through the channel. In some embodiments, a device for delivering an agent to a treatment site may by adapted to perform such a method.

In some embodiments, the method may include: forming in a myocardium a channel and a check valve that has a cracking pressure; and injecting a fluid comprising therapeutic cells into the myocardium via the channel at a pressure that is higher than the cracking pressure. In some embodiments, a device for delivering an agent to a treatment site may by adapted to perform such a method.

In some embodiments, the method may include: puncturing a channel in a myocardium; and cutting the myocardium to partially detach a section of the myocardium that impedes backflow of therapeutic cells delivered through the channel. The partially detached section may include one or more tissue flaps, for example. In some embodiments, a device for delivering an agent to a treatment site may by adapted to perform such a method.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

FIG. 27 shows the delivery device of FIG. 21 in a different state of operation;

FIG. 28 shows an enlarged view of the delivery device of FIG. 27;

FIG. 29 shows a side view of the delivery device of FIG. 27;

FIG. 30 shows a top view of the delivery device of FIG. 27;

FIG. 31 shows a cross-sectional view of the delivery device taken along the line 31-31 of FIG. 30;

FIG. 32 shows an enlarged view of the delivery device of FIG. 31;

DETAILED DESCRIPTION OF THE EMBODIMENTS

Figures 1, 2:
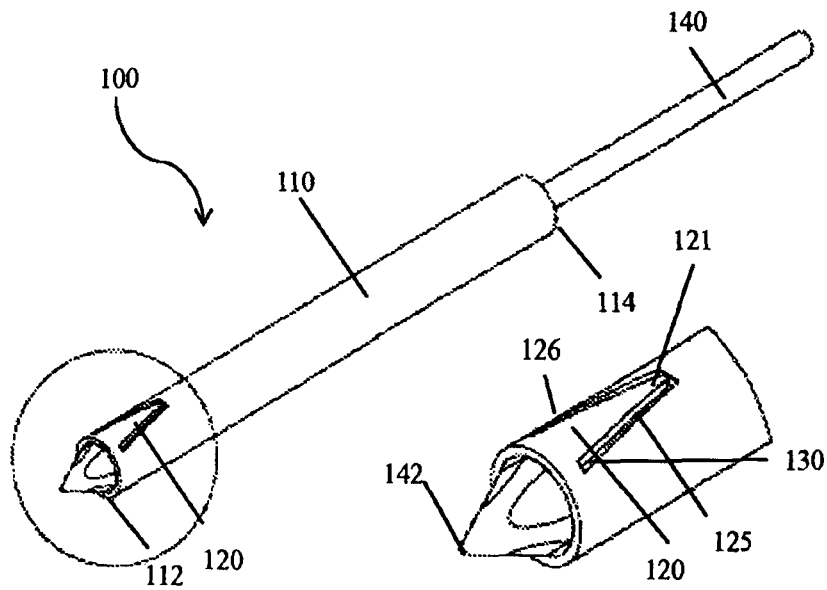
FIG. 1 shows a delivery device according to embodiments.
FIG. 2 shows an enlarged view of the delivery device of FIG. 1.
Figure 3:
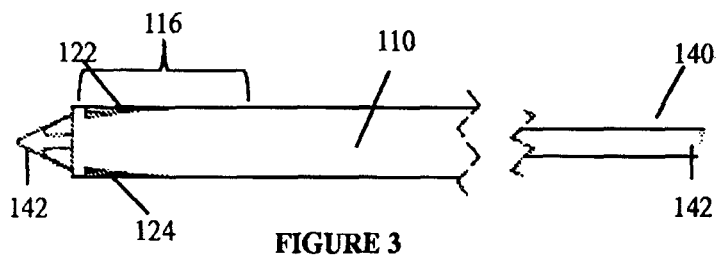
FIG. 3 shows a side view of the delivery device of FIG. 1.
Figure 4:
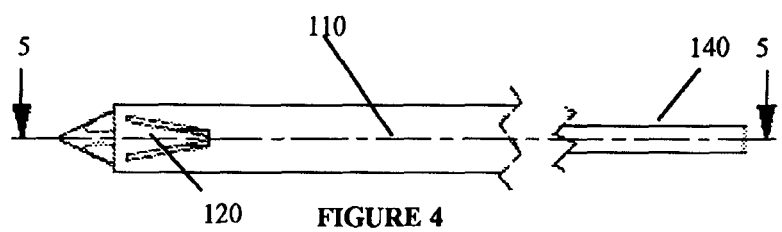
FIG. 4 shows a top view of the delivery device of FIG. 1.
Figure 5:
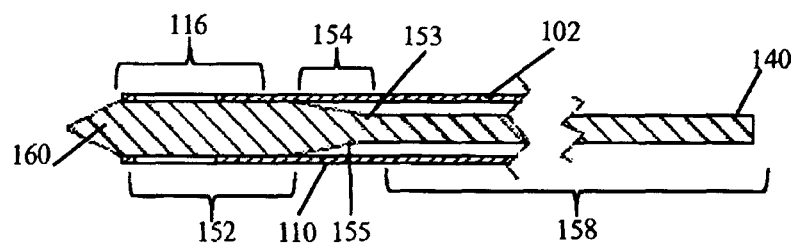
FIG. 5 shows a cross-sectional view of the delivery device taken along the line 5-5 of FIG. 4.

The following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications.

It will be understood that the delivery devices according to the embodiments may be implanted into a patient with use of a delivery system. Implantation may be fully manual, machine implemented or controlled, or accomplished with a combination of manual and machine intervention. The delivery devices may be a part of the delivery system. Delivery may be fully manual, machine implemented or controlled, or accomplished with a combination of manual and machine intervention. The proximal end (not shown in detail) of the disclosed delivery devices may be attached or connected to the delivery system, e.g. as a component thereof. The disclosed delivery devices may be either part of the main body of the delivery system or may be a detachable component. The delivery system may be any known delivery system configured to advance and control the advancement of the delivery device to the treatment site. The delivery system may include but is not limited to a handle assembly, an introducer, and a guide wire. The delivery systems are not limited to those shown in the figures, and the delivery devices may be used with other delivery systems. It will also be understood that a clinician may use a delivery system to control the operation of the disclosed delivery devices. Further, the delivery systems may be computer controlled in part or in whole. It will be further understood that although the operations of the disclosed delivery devices are discussed with respect to the actions of a clinician, delivery systems may be configured to perform these actions.

The delivery systems and the disclosed devices may be adjusted and sized for the anatomy and the direction of the desired point of insertion. For example, the delivery systems and devices may be sized for lengthwise insertion into a vascular lumen (e.g., 1.0-2.0 mm in diameter). The disclosed delivery systems and devices may also be adjusted according to the requirements of the therapeutic agent(s) to be delivered to the patient. The requirements may include, but not limited to, the size and the dosage amount of the therapeutic agent(s).

The delivery devices and systems according to embodiments may be configured to deliver a therapeutic agent(s). The "therapeutic agent" may include any one or more substance, compound, composition, formulation, and/or agent capable of exerting an effect, such as a therapeutic, prophylactic or diagnostic effect, on a patient.

The therapeutic agent can include one or more therapeutic cells, such as stem cells, progenitor cells, cells having a capability to differentiate into a specific type of cell, or cells emitting or triggering emission of a healing biochemical after delivery into a patient. Such therapeutic cells may be carried in a liquid and/or combined with one or more other therapeutically effective agents. Therapeutic cell(s) (or other therapeutic agents) may be embedded or dispersed in alginate strings or filaments, encapsulated, suspended in a highly viscous solution, suspended in a high-volume fraction solution (e.g., saline solution), as well as provided in any known vehicle to deliver a therapeutic agent. Such strings or filaments may be end loaded into the distal end of the delivery devices and systems according to embodiments, without necessarily feeding from the proximal end to the distal end. Suitable techniques for making therapeutic agent(s), for example, making strings and filaments comprising cells and alginate, are known in the art and may be readily created by those of ordinary skill having benefit of the present teaching. See, for example, "Grafting microcapsules of genetically modified cells: Therapeutic potential in spinal cord injury;" M. Wheatley, N. Dhoot, S. Kanakasabai and I. Fischer; Drexel University, Philadelphia, USA; XVth International Workshop on Bioencapsulation, Vienna, Au.; Sep. 6-8, 2007; S7-2, pages 1-4.

The terms "distal" and "proximal" used herein with respect to the delivery device and features are with respect to the position of the delivery device when in use. "Distal" indicates an end of the delivery device or a feature of the device closest to, or a direction towards the treatment site, and "proximal" indicates an end of the device or a feature of the device farthest from, or a direction away from the treatment site. "Treatment site" refers to any site or region of a subject, human or animal, intended to be treated, such as a tissue of an organ or muscle.

The delivery systems, devices and methods according to embodiments address potentially problematic, and perhaps deleterious, leakage or escape of therapeutic agents from the treatment site during or after the delivery of the agents by a conventional delivery device. A conventional delivery device can form a puncture or needle track in a tissue after the device has been removed from the tissue after the injection of an agent. For example, with respect to soft tissue, the injected agent can push the elastic soft tissue aside thereby forming a "pocket" as it is injected. The soft tissue can expand in order to accommodate the volume of agent injected. Because the tissue is elastic, the pressure in the bolus of the injected agent can rise and when the conventional delivery device is withdrawn, there is a tendency for the agent to be expelled from the tissue along the puncture track.

A delivery device according to embodiments may increase the retention of the therapeutic agent, and thereby increase the effective dose of agents delivered, because the delivery device is configured to generate pressure in the treatment site before (or in the advance of) or at the time of the delivery of the agents to prevent the leakage of the agent after delivery. As will be discussed in further detail below, the pressure can close a channel to impede backflow. According to some embodiments, one or more valves formed in tissue can promote agent retention, and such a valve may be characterized as one or more of a check valve, a non-return valve, and a stop valve. A delivery device according to the embodiments thus may reduce the difficulties with delivering therapeutic agents.

Additionally, delivery systems, devices and methods according to some embodiments can manage shear stress associated with delivering agents through conventional needles. Conventional needles may subject an agent to problematic levels of shear stress when the agent travels through a needle's narrow internal channel. A delivery device according to some embodiments may reduce or eliminate shear stress associated with the delivery of an agent, because with enhanced retention of the agent, the amount or volume of agent delivered can be reduced. Reduced volume results in reduced flow rate and thus reduced shear stress. Further, the structure of the delivery device can be configured to reduce resistance during the delivery.

A delivery device according to embodiments may be configured to form at least one "channel" at the treatment site. The channel may be formed by puncturing or separating tissue at the treatment site, for example, by cutting the tissue and/or partially or entirely coring the tissue at the treatment site and/or piercing the tissue. The channel(s) may include at least one delivery channel into which an agent may delivered by the delivery device and/or at least one (pressure) channel configured to generate pressure at the treatment site.

FIGS. 1 through 42N show examples of the delivery devices and systems that are configured to enhance retention of delivered agents and that may include sheaths, elongate members, and operation thereof, according to different embodiments. It will be understood that the delivery devices are not limited to the configuration and/or combination of the sheath and/or elongate member shown in the figures. The delivery devices may include any combination of the embodiments of the sheath and the elongate member. Moreover, delivery devices and systems in accordance with some disclosed embodiments, may be configured for agent retention without a sheath and/or elongate member.

FIGS. 1 through 10 show a delivery device 100 according to some embodiments. In some embodiments, the delivery device 100 may include a sheath 110. The delivery device 100 may also include an elongate member 140 configured to be movable with respect to the sheath 110.

In some embodiments, the sheath 110 may include a first (distal) end 112, an opposing second (proximal) end 114, and a length therebetween. The sheath 110 may include an inner channel or lumen 102 that extends along its length between the first end 112 and the second end 114.

In some embodiments, the sheath 110 may have a substantially uniform cylindrical shape along its length. In some embodiments, the sheath 110 may have the same outer diameter along its length. In other embodiments, the sheath 110 may have different shapes or diameters along its length.

In some embodiments, as an alternative to extending lengthwise, the sheath 110 may be a thin band. In some embodiments, the sheath 110 may only partially circumscribe the elongate member 140. For example, a slot may extend longitudinally throughout the sheath 110.

In some embodiments, the sheath 110 may include an opening disposed at each of the ends. In some embodiments, the sheath 110 may include a plurality of sections. The sections may be made of the same or different materials. In some embodiments, the sections may be made of a same material but at least one of the sections may have different properties, such as, elastic properties. In some embodiments, one or more of the sections may be made of a flexible material.

The materials may include but are not limited to one or more the following materials: metallic alloys, shape memory alloy (e.g., Nitinol), thermoplastic elastomer, urethane, polymer, polypropylene, plastic, ethylene chlorotrifluoroethylene (ECTFE), polyterafluoroethylene (PTFE), fluorinated ethylene propylene copolymer (FEP), nylon, resin, polyurethane, combinations thereof, and the like.

In some embodiments, one of the sections the sheath 110 may include at least one reversibly depressible or collapsible section (hereinafter referred to as "depressible") 116 disposed along its length. In some embodiments, the sheath 110 may include more than one depressible section 116 disposed along its length. The depressible section 116 may be configured to move between a first (aligned) position as shown in FIGS. 1 through 5 and a second (depressed) position as shown in FIGS. 6 through 10. The aligned position may include when the depressible section 116 is substantially aligned with the outer diameter, for example, as shown in FIGS. 1 through 5. The depressed position may include when the depressible section 116 is depressed into the inner channel 102, for example, as shown in FIGS. 6 through 10. The depressible section 116 may be configured to depress to a second diameter that is smaller than the outer diameter. The term "diameter," as used herein, refers to the length of a line passing from side to side through a figure, body, or object, whether such an object has a cross section that is circular, oval, elliptical, square, or other appropriate geometric form.

In some embodiments, the movement of the depressible section 116 from the aligned and depressed positions may be based on the movement or position of an elongate member with respect to the sheath 110. The depressible section 116 may be configured to depress or collapse from the outer or first diameter into the inner channel 102 when not supported, for example, by the elongate member. The movement of the depressible section 116 between the two positions may be strained induced, for example mechanical strain in the depressible cross section may produce the deformed section. Mechanical strain induced in the depressible section 116 as a result of its being depressed may be made to cause movement of one or more penetrating members 120 from closed to protruding positions. (See also, for example, penetrating members 1120 and 2120 in the embodiments shown in FIGS. 16 and 27, and elsewhere.)

In some embodiments, the depressible section 116 may be disposed at an end of the sheath 110. As shown in FIGS. 1 through 10, the depressible section 116 may be disposed at the first end 112. However, it will be understood that the depressible section 116 is not limited to this location. In other embodiments, the depressible section 116 may be disposed at other positions along the length of the sheath 110.

In some embodiments, the sheath 110 may include at least one penetrating member 120 disposed along its length. The at least one penetrating member 120 may be configured to reversibly move between a first (aligned) or closed position as shown in FIGS. 1 through 5 and a second (protruded) or opened position as shown in FIGS. 6 through 10. In aligned position, the penetrating member 120 may be substantially aligned with the outer diameter of the sheath 110. In the protruded position, the penetrating member 120 may protrude at an angle from the outer diameter toward the first end 112 or second end 114 of the sheath 110 when in the protruded or open position. The penetrating member 120 may be configured to protrude from the sheath 110 at any angle. In some embodiments, the angle of protrusion may be about 45 degrees or less. In other embodiments, the angle of protrusion may be more than 45 degrees.

In some embodiments, the movement of the penetrating member 120 may depend on the position or state of the depressible section 116. For example, when the depressible section 116 is in the first or aligned position, the penetrating member 120 may be in the first or aligned position as shown in FIGS. 1 through 5. The penetrating member 120 may be in the second or protruded position as shown in FIGS. 6 through 10 when the depressible section 116 is in the second or depressed position.

In some embodiments, the sheath 110 may include one penetrating member 120 (122, 124). In other embodiments, the sheath 110 may include more than one penetrating member 120. As shown in FIGS. 1 through 10, the sheath 110 may include two penetrating members 122 and 124. In other embodiments, the sheath 110 may include more than two penetrating members 120, or only one penetrating member 120.

In some embodiments, the penetrating member(s) 120 may be disposed at the depressible section 116. In other embodiments, the penetrating member(s) 120 may be disposed at other positions along the length of the sheath 110. For example, the location of the penetrating member(s) 120 is not limited to the position with respect to the sheath 110 as shown in FIGS. 1 through 10. The penetrating member(s) and the depressible section 116 may be disposed at another location along the length of the sheath 110.

In some embodiments, the penetrating members 120 may be evenly spaced along the circumference of the sheath 110 at a position along its length. In other embodiments, the penetrating members 120 may be staggered along the length and/or circumference of the sheath 110.

In some embodiments, the penetrating member(s) 120 may each include at least one puncture member 121 configured to penetrate into the treatment site to form a channel in tissue at the treatment site when the penetrating member(s) 120 is in a protruded position, as shown in FIGS. 6 through 10. The channel may be a delivery channel into which an agent may delivered by the delivery device and/or a pressure channel. In some embodiments, the penetrating member(s) 120 may be configured to form at least one pressure channel surrounding a delivery channel. In some embodiments, the puncture member 121 may be configured to core tissue rather than separating the tissue without coring at the treatment site. In some embodiments, the puncture member 121 may be configured to partially or entirely core tissue at the treatment site.

In some embodiments, the puncture member 121 may include a puncture tip 123. In some embodiments, the puncture member 121 may additionally or alternatively include at least one puncture edge. In some embodiments, the puncture member 121 may include two puncture edges 125 and 126. In some embodiments, the two puncture edges 125 may include cutting edges, and the two puncture members 121 may be viewed as and/or include knife or scalpel-like blades. The puncture member 121 may be configured to produce a circumscribing cut that forms a conical or tapering structure in tissue when rotated, as will be discussed in further detail below with reference to FIGS. 42A-N.

In some embodiments, the penetrating member(s) 120 may have a triangular shape, as shown in FIGS. 1 through 10. In other embodiments, the penetrating member(s) 120 may have a different shape. In some embodiments, the penetrating member(s) 120 may be disposed so that the puncture member 121 protrudes from the outer diameter toward the second (proximal) end 114 of the sheath 110, as shown in FIGS. 5 through 10. Thus, the deployed puncture member 121 may be oriented away from the leading tip of the delivery device 100. In other embodiments, the penetrating member 120 may be disposed so that the penetrating member 120 protrudes from the outer diameter toward the first (distal) end 112 when in the protruded or open position. Thus, in certain embodiments, the deployed puncture member 121 may, as an alternative to the configuration shown in FIGS. 1-10, be oriented towards the leading tip of the delivery device 100.

In some embodiments, the penetrating member(s) 120 may have the same size, shape, and/or disposition. In other embodiments, the penetrating member(s) 120 may have a different size, shape and/or disposition.

In some embodiments, the sheath 110 may include at least one opening 130 disposed along its length. In some embodiments, the at least one opening 130 may be configured to deliver a therapeutic agent.

Figures 6, 7:
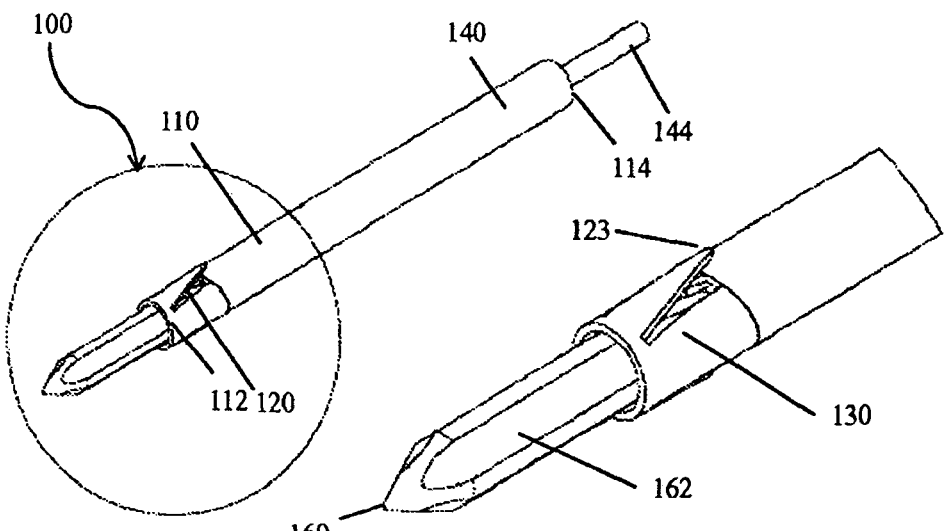
FIG. 6 shows the delivery device of FIG. 1 in a different state of operation.
FIG. 7 shows an enlarged view of the delivery device of FIG. 6.
Figure 8:
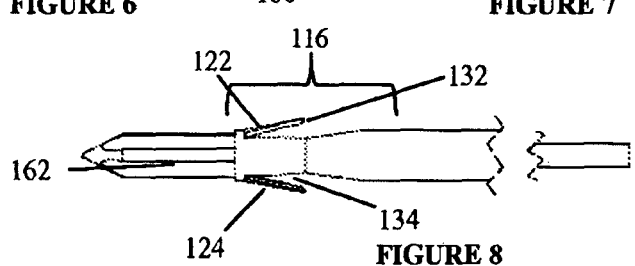
FIG. 8 shows a side view of the delivery device of FIG. 6.
Figure 9:
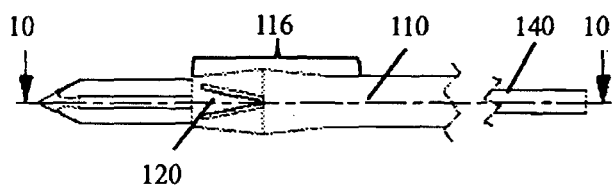
FIG. 9 shows a top view of the delivery device of FIG. 6.
Figure 10:
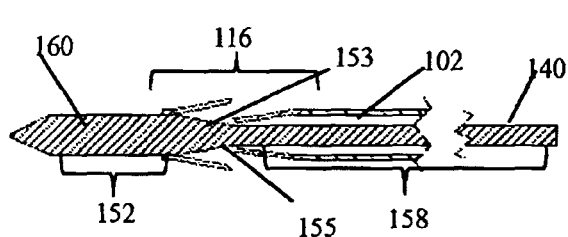
FIG. 10 shows a cross-sectional view of the delivery device taken along the line 10-10 of FIG. 9.
Figure 11:
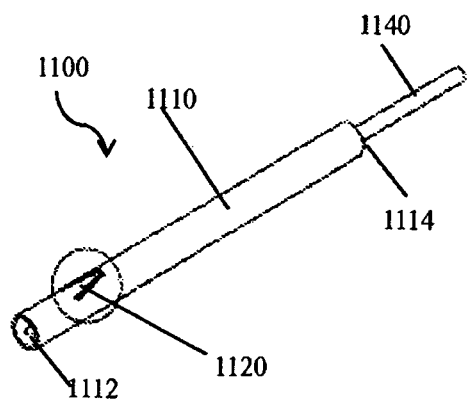
FIG. 11 shows a delivery device according to embodiments.
Figure 12:
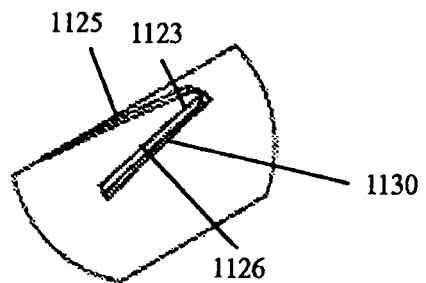
FIG. 12 shows an enlarged view of the delivery device of FIG. 11.
Figure 13:
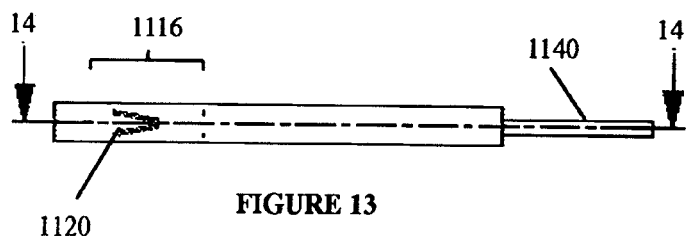
FIG. 13 shows a top view of the delivery device of FIG. 11.
Figure 14:
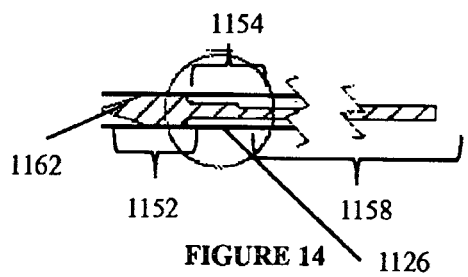
FIG. 14 shows a partial cross-sectional view of the delivery device taken along the line 14-14 of FIG. 13.
Figure 15:
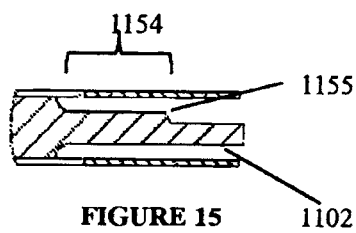
FIG. 15 shows an enlarged view of the delivery device of FIG. 14.
Figure 16:
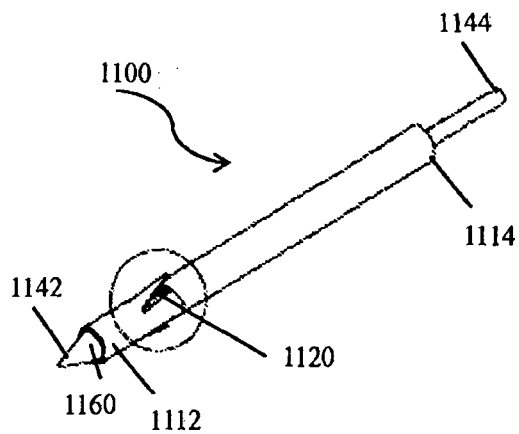
FIG. 16 shows the delivery device of FIG. 11 in a different state of operation.

In some embodiments, the penetrating member(s) 120 (122, 124) may be disposed within each opening 130. The shape, disposition, and/or number of the opening(s) 130 may correspond to the shape, disposition and/or number of penetrating member(s) 120. As shown in FIGS. 7 and 8, the sheath 110 may include openings 132 and 134. The openings 132 and 134 may have a corresponding triangular shape. In other embodiments, the penetrating member(s) include other shaped or no opening(s).

In some embodiments, the sheath 110 may include a coating on the outer surface to aid the placement of the sheath 110. For example, the outer surface may be treated with active agents to prevent platelet adhesion or aggregation and blood clot formation, such as an anti-coagulant coating; a lubricant, such as a water-based, water-soluble lubricant; other materials, such as radiopaque coating material; or a combination thereof.

In some embodiments, the elongate member 140 may be configured to move with respect to the sheath 110. The elongate member 140 may be configured to cause the depressible section 116 and/or the penetrating member(s) 120 to move between the first and second positions. The position(s) of the depressible section 116 and the penetrating member(s) 120 may depend on the position of the elongate member 140 with respect to the sheath 110.

The elongate member 140 may be made of any known biocompatible material. The material may be rigid and/or flexible. In some embodiments, the materials may include but are not limited to one or more the following materials: metallic alloys, shape memory alloy (e.g., Nitinol), thermoplastic elastomer, urethane, polymer, polypropylene, plastic, ethylene chlorotrifluoroethylene (ECTFE), polyterafluoroethylene (PTFE), fluorinated ethylene propylene copolymer (FEP), nylon, resin, polyurethane, combinations thereof, and the like.

In some embodiments, the elongate member 140 may be rigid in at least one direction. In some embodiments, the elongate member 140 may be radially rigid. In other embodiments, the elongate member 140 may be entirely or partially flexible in at least one direction. In some embodiments, a portion of the elongate member 140 along its length may be flexible.

In some embodiments, the elongate member 140 may include a first (distal) end 142, an opposing second (proximal end) 144, and a length therebetween. In some embodiments, the elongate member 140 may be concentric partially or entirely along its length. In other embodiments, the elongate member 140 may have a different shape.

In some embodiments, the elongate member 140 may be partially or completely solid. In other embodiments, the elongate member 140 may be partially or completely hollow.

In some embodiments, the elongate member 140 may have a diameter that varies along its length. The diameters may be configured to control the movement of the depressible section 116 and/or penetrating member(s) 120 of the sheath 110. The diameters of the elongate member 140 may depend on the location of the depressible section and/or configuration of the sheath 110.

In some embodiments, at least one of the diameters of the elongate member 140 may be configured to support the depressible section 116 to maintain the penetrating member 120 in the aligned position when positioned adjacent to the depressible section 116. At least another one of the diameters may be configured to support the depressible section 116 to maintain the penetrating member 120 in a protruded position when positioned adjacent to a portion of the depressible section 116.

In other embodiments, the elongate member 140 may have the same diameter along its length.

In some embodiments, the elongate member 140 may include more than one section. The elongate member 140 may include any number of sections. In some embodiments, the elongate member 140 may include at least a first section 152, a second section 154, and a third section 158. In some embodiments, the elongate member 140 may include more or less sections.

In some embodiments, at least a portion of the first section 152 may be configured to support the depressible section 116 to maintain the penetrating member(s) 120 in the aligned position when positioned adjacent to the depressible section 116. The first section may have a first diameter along partially or entirely along the length of the first section. The first diameter 152 may substantially correspond to the inner diameter of the sheath 110. The first diameter, however, may be slightly smaller than the inner diameter of the sheath 110 to allow movement of the elongate member 140 within the inner channel 102. In some embodiments, the first diameter may be configured to substantially prevent a therapeutic agent and/or a medical fluid from flowing through the inner channel 102.

In some embodiments, at least a portion of the second section 154 may be configured to support the depressible section 116 in the depressed position to maintain the penetrating member 120 in the protruded position when positioned adjacent to a portion of the depressible section 116. The second section 154 may have a second diameter that is less than the first diameter. In some embodiments, the second section 154 may have a tapered diameter partially or entirely along the length and/or circumference of the second section 154. In some embodiments, the tapered diameter may be symmetric as shown in FIGS. 1 through 10. In other embodiments, the tapered diameter may be asymmetric. The tapering of the diameter may be based on the length and shape of the penetrating member 120.

In some embodiments, the elongate member 140 may include at least one tapered surface configured to support the depressible section 116. In some embodiments, the tapered surface may be configured to control the delivery of a therapeutic agent from the delivery device 100.

As shown in FIGS. 1 through 10, in some embodiments, the elongate member 140 may include two substantially symmetric tapered surfaces 153 and 155. The surfaces 153 and 155 may be disposed at the second section 154. In other embodiments, the elongate member 140 may include asymmetric tapered surfaces.

In some embodiments, the tapered surfaces 153 and 155 may be configured to support a portion of the depressible section 116 when disposed adjacent thereto. In some embodiments, the tapered surfaces 153 and 155 may be configured to restrain the depression of the depressible section 116, and thereby may be configured to control the amount of protrusion of the penetrating member 140 and/or the size of the opening 130.

In some embodiments, the third section 158 may have a third diameter that is less than the first diameter and the second diameter. The third section 158 may be parallel to the first section 154. The third diameter may be configured to allow flow of a therapeutic agent and/or another medical fluid through the inner channel 102 of the sheath 110.

In some embodiments, the elongate member 140 may be configured to create at least one delivery channel at the treatment site by cutting or piercing the tissue to separate the tissue at the treatment site. In some embodiments, the elongate member 140 may include at least one puncture member 160 configured to penetrate the treatment site to form a delivery channel for the agent to be delivered by the delivery device. In some embodiments, the puncture member 160 may be configured to separate tissue rather than core the tissue at the treatment site. In other embodiments, the puncture member 160 may be configured to partially or entirely core tissue at the treatment site.

In some embodiments, a puncture member 160 may be disposed at the first end 142. In other embodiments, the elongate member 140 may include additional puncture member(s) disposed along its length. For example, the elongate member 140 may include one, two, three, or more than three puncture members along its length. The puncture members may have the same or different shape and/or configuration.

In some embodiments, the puncture member 160 may include a sharp tip or blunt tip. In some embodiments, the sharpness of the puncture member 160 may depend on the tissue of the treatment site.

In some embodiments, the puncture member 160 may have a conical shape as shown in FIGS. 1 through 10. In other embodiments, the puncture member 160 may have a different shape. In some embodiments, the puncture member 160 may have single faceted, multi-faceted shape, conical shape, or a combination thereof. The shape of the puncture member 160 may depend on any one of the sheath, tissue type, location, and access path of the treatment site.

In some embodiments, the elongate member 140 may be configured to deliver a therapeutic agent. The elongate member 140 (or one or more other elements of the delivery device 100) may be fluted. In some embodiments, the elongate member may include at least one groove 162 disposed partially or entirely along its length. The elongate member 140 may include a plurality of grooves 162. As shown in FIGS. 1 through 10, the elongate member 140 may include four grooves 162. In other embodiments, the elongate member 140 may include more or less grooves 162.

In some embodiments, the groove(s) 162 may be configured to deliver a therapeutic agent. The groove(s) 162 may be configured to allow the flow of a therapeutic agent and/or any known fluid through the inner channel 102 and across the first section of the elongate member 140. In some embodiments, the elongate member 140 may be configured to deliver a therapeutic agent when the depressible section 116 and the penetrating member 120 are in the depressed and protruded positions, respectively.

In other embodiments, the elongate member 140 may not include or omit the channel 162. In some embodiments, the penetrating member 120 may be configured to alternatively or additionally deliver a therapeutic agent.

In operation, the clinician may position the delivery device 100 at the treatment site intended to be treated, such as a diseased tissue. The delivery device 100 may be positioned at the treatment site while the depressible section 116 is in a first or aligned position, as shown in FIGS. 1 through 5. Working from the proximal end 114 of the delivery device 100, the clinician may maintain the sheath 110 in a fixed position and move the elongate member 140 forward further toward the treatment site so that a portion of the elongate member 140 extends from the distal end 112, as shown in FIGS. 6 through 10. While the elongate member 140 is being moved towards the distal end 112 of the delivery device 100, the depressible section 116 may move into the second or depressed position, causing the penetrating member(s) 120 (122, 124) to move into the second or protruded position to penetrate or cut tissue at the treatment site. In the second position, the penetrating member(s) 120 and/or elongate member 140 may form channels at the treatment site. If additional channels are desired, the clinician may retract the elongate member 140 toward the proximal end 114 so that the depressible section 116 moves into the aligned position and then may rotate the sheath 110, for example, 90 degrees, and repeat the process to penetrate the tissue at different locations at the treatment site. After a desired number of channels are formed by the penetrating member(s) 120, the clinician may cause the delivery device 100 to deliver a therapeutic agent.

Because the penetrating member(s) 120 are configured to form at least one pressure channel, the generated pressure at the treatment site may cause the cuts in the tissue to push tissue flaps together when the elongate member 140 is retracted after the agent is delivered, thereby preventing the agent from leaking along the path of the delivery device 100 as it is removed.

In some embodiments, the penetrating member(s) 120 (122, 124) may be configured to deliver a therapeutic agent, for example via including a channel or lumen in one or more of the penetrating member(s) 120 (122, 124. FIGS. 11 through 32 show examples of delivery devices according to these embodiments.

As discussed above, the penetrating member(s) 120 (122, 124) of the delivery device 100 may be configured to deploy in response to linear motion of the elongate member 140. Alternatively, the penetrating member(s) 120 (122, 124) may be configured to deploy in response to rotation of the elongate member 140. Other mechanisms are also available for deploying and retracting the penetrating member(s) 120 (122, 124). For example, the penetrating member(s) 120 (122, 124) may be configured to be controlled by one or more springs, by release of energy from a tensioned elastic (e.g. rubber) band or similar element, by motor, by solenoid, by gears, by pulleys, by a lead screw, by heat, by chemical energy, by electricity, or other appropriate mechanism available in the art. In some embodiments, a wire or thin cable may be configured to control opening and closing of the penetrating member(s) 120 (122, 124). For example, the clinician may pull a wire or cable to a first position, where the wire or cable transfers force to the penetrating member(s) 120 (122, 124) to open them. A second pull can retract the penetrating member(s) 120 (122, 124) to the closed position. In some embodiments, the penetrating member(s) 120 (122, 124) may be configured to be opened and closed using hydraulics, driven proximally by hand or pump, for example. Accordingly, the delivery device 100 shown in FIGS. 1-10 as well as the other delivery devices and systems discussed below, are amenable to a wide variety of means, mechanisms, and technology for controlling distal motion of a catheter or other invasive or interventional device.

The delivery device shown in FIGS. 1 through 10 may be modified to deliver therapeutic agent over the penetrating member(s) 120 (122, 124) according to any one of these embodiments. It would be understood that the embodiments of the sheath, the elongate member, and the delivery device described with respect to FIGS. 1 through 10 may also apply to the sheaths, elongate members, and delivery devices described with respect to FIGS. 11 through 32. The sheaths, elongate members, and delivery devices described with respect to FIGS. 11 through 32 may be similar with some respects to the sheath, the elongate member, and the delivery device described with respect to FIGS. 1 through 10. It will also be understood that the configurations of sheaths and elongate members shown in FIGS. 11 through 32 are not limited to those shown in the figures and may include other configurations.

As shown in FIGS. 11 through 20, a delivery device 1100 may include a sheath 1110. The delivery device 1100 may also include an elongate member 1140 configured to be movable with respect to the sheath 1110.

In some embodiments, like the sheath 110, the sheath 1110 may include a first (distal) end 1112, an opposing second (proximal) end 1114, and a length therebetween. The sheath 1110 may include an inner channel or lumen 1102 that extends along its length between the first end 1112 and the second end 1114. In some embodiments, the sheath 1110 may include an opening disposed at each of the ends.

In some embodiments, the sheath 1110 may have a substantially uniform cylindrical shape along its length. In some embodiments, the sheath 1110 may have the same outer diameter along its length. In other embodiments, the sheath 1110 may have different shapes or diameters along its length.

In some embodiments, the sheath 1110 may include a plurality of sections. The sections may be made of the same or different materials. In some embodiments, the sections may be made of a same material but at least one of the sections may have different properties, such as, elastic properties. In some embodiments, one or more of the sections may be made of a flexible material.

The materials may include but are not limited to one or more the following materials: metallic alloys, shape memory alloy (e.g., Nitinol), thermoplastic elastomer, urethane, polymer, polypropylene, plastic, ethylene chlorotrifluoroethylene (ECTFE), polyterafluoroethylene (PTFE), fluorinated ethylene propylene copolymer (FEP), nylon, resin, polyurethane, combinations thereof, and the like.

In some embodiments, like the sheath 110, one of the sections the sheath 1110 may include at least one reversibly depressible or collapsible section (hereinafter referred to as "depressible") 1116 disposed along its length. In some embodiments, the sheath 1110 may include more than one depressible section 1116 disposed along its length. The depressible section 1116 may be configured to move between a first (aligned) position as shown in FIGS. 11 through 15 and a second (depressed) position as shown in FIGS. 16 through 20. The aligned position may include when the depressible section 1116 is substantially aligned with the outer diameter, for example, as shown in FIGS. 11 through 15. The depressed position may include when the depressible section 1116 is depressed into the inner channel 1102, for example, as shown in FIGS. 16 through 20.

In some embodiments, the movement of the depressible section 1116 from the aligned and depressed positions may be based on the movement or position of an elongate member 1140 with respect to the sheath 1110. The depressible section 1116 may be configured to depress or collapse from the outer or first diameter into the inner channel 1102 when not supported, for example, by the elongate member. The movement of the depressible section 1116 between the two positions may be strained induced.

The depressible section 1116 may be disposed between the first end 1112 and the second end 1114. In some embodiments, the depressible section 1116 may be disposed closer to the first end 1112 than the second end 1114. For example, the depressible section 1116 may be disposed about ⅓ or ¼ along the length from the first end toward the second end. However, it will be understood that the depressible section 1116 is not limited to this location. In other embodiments, the depressible section 1116 may be disposed at other positions along the length of the sheath 1110.

In some embodiments, like the sheath 110, the sheath 1110 may include at least one penetrating member 1120 disposed along its length. The at least one penetrating member 1120 may be configured to reversibly move between a first (aligned) or closed position as shown in FIGS. 11 through 15 and a second (protruded) or opened position as shown in FIGS. 16 through 20. In aligned position, the penetrating member 1120 may be substantially aligned with the outer diameter of the sheath 1110. In the protruded position, the penetrating member 1120 may protrude from the outer diameter at an angle. The penetrating member 1120 may protrude from the outer diameter toward the first end 1112 or second end 1114 of the sheath 1110 when in the protruded or open position. The penetrating member 1120 may be configured to protrude from the sheath 1110 at any angle. In some embodiments, the angle of protrusion may be about 45 degrees or less. In other embodiments, the angle of protrusion may be more than 45 degrees.

In some embodiments, the movement of the penetrating member 1120 may depend on the position or state of the depressible section 1116. For example, when the depressible section 1116 is in the first or aligned position, the penetrating member 1120 may be in the first or aligned position as shown in FIGS. 11 through 15. The penetrating member 1120 may be in the second or protruded position as shown in FIGS. 16 through 20 when the depressible section 1116 is in the second or depressed position.

In some embodiments, the sheath 1110 may include one penetrating member 1120. In other embodiments, the sheath 1110 may include more than one penetrating member 1120 (1122 and 1124). As shown in FIGS. 11 through 20, the sheath 1110 may include two penetrating members 1120. In other embodiments, the sheath 1110 may include more than two penetrating members 1120.

In some embodiments, the penetrating member(s) 1120 may be disposed at the depressible section 1116. In other embodiments, the penetrating member(s) 1120 may be disposed at other positions along the length of the sheath 1110. For example, the location of the penetrating member(s) 1120 is not limited to the position with respect to the sheath 1110 as shown in FIGS. 11 through 20. The penetrating member(s) 1120 and the depressible section 1116 may be disposed at other location(s) along the length of the sheath 1110.

In some embodiments, the penetrating member(s) 1120 may be evenly spaced along the circumference of the sheath 1110 at a position along its length. In other embodiments, the penetrating member(s) 1120 may be staggered along the length and/or circumference of the sheath 1110.

In some embodiments, the penetrating member(s) 1120 may each be longer than the outer diameter of the delivery device 1100. In some embodiments, when deployed, the penetrating member(s) 1120 may each be at least three times the outer diameter of the delivery device 1100. In some embodiments, the penetrating member(s) 1120 may have lengths that are selected according to the type of tissue in which the therapeutic agent is to be deployed, and/or selected according to the type of therapeutic agent.

In some embodiments, the penetrating member(s) 1120 may include at least one puncture member 1123, such as a puncture tip, configured to penetrate into the treatment site to form a channel in tissue at the treatment site when the penetrating member(s) 1120 is in a protruded position, as shown in FIGS. 16 through 20. In some embodiments, the puncture member 1123 may be configured to separate tissue rather than core the tissue at the treatment site. In other embodiments, the puncture member 1123 may be configured to partially or entirely core tissue at the treatment site.

In some embodiments, the puncture member 1123 may include a puncture tip. In some embodiments, the puncture member 1123 may additionally or alternatively include at least one puncture edge. In some embodiments, the puncture member 1123 may include two puncture edges 1125 and 1126, which may be sharpened to facilitate cutting tissue.

In some embodiments, the penetrating member(s) 1120 may have a shape similar to the penetrating member(s) 120. The penetrating member(s) 1120 may have a triangular shape, as shown in FIGS. 11 through 20. In other embodiments, the penetrating member(s) 1120 may have a different shape. In some embodiments, the penetrating member(s) 1120 may be disposed so that the puncture member 1123 protrudes from the outer diameter toward the second end 1114 of the sheath 1110, as shown in FIGS. 11 through 15. In other embodiments, the penetrating member 1120 may be so that the penetrating member 1120 protrudes at an angle from the outer diameter toward the first end 1112 when in the protruded or open position.

In some embodiments, the penetrating member(s) 1120 may have the same size, shape, and/or disposition. In other embodiments, the penetrating member(s) 1120 may have a different size, shape and/or disposition.

In some embodiments, the sheath 1110 may include at least one opening 1130 disposed along its length. In some embodiments, the at least one opening 1130 may be configured to deliver a therapeutic agent, for example, when the penetrating member 1120 is in the protruded or open position.

In some embodiments, the penetrating member(s) 1120 may be disposed within each opening 1130. The shape, disposition, and/or number of the opening(s) 1130 may correspond to the shape, disposition and/or number of penetrating member(s) 1120.

Figure 17:
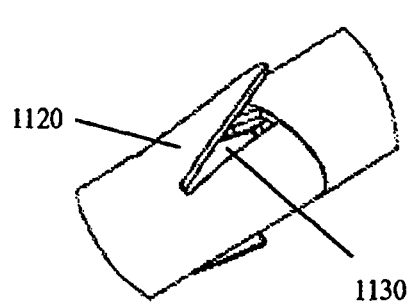
FIG. 17 shows an enlarged view of the delivery device of FIG. 16.
Figure 18:
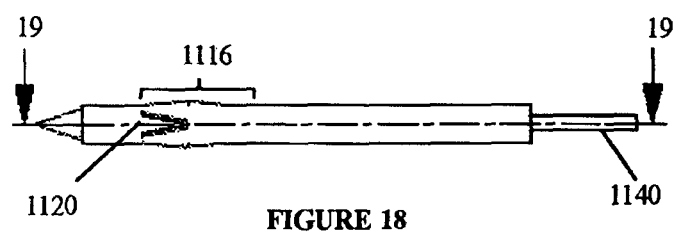
FIG. 18 shows a top view of the delivery device of FIG. 16.

As shown in FIGS. 17 and 18, the sheath 1110 may include two openings 1130 and 1132. The openings 1130 and 1132 may have a corresponding triangular shape. The openings 1130 and 1132 may have the same size, shape and/or disposition and may be diametrically opposed or offset from diametric opposition. In other embodiments, the opening(s) 1130, 1132 may have a different size, shape and/or disposition.

In some embodiments, the sheath 1110 may include a coating on the outer surface to aid the placement of the delivery device 1100. For example, the outer surface may be treated with active agents to prevent platelet adhesion or aggregation and blood clot formation, such as an anticoagulant coating; a lubricant, such as a water-based, water-soluble lubricant; other materials, such as radiopaque coating material; or a combination thereof.

In some embodiments, the elongate member 1140 may be configured to move with respect to the sheath 1110. The elongate member 1140 may be configured to cause the depressible section 1116 and/or the penetrating member(s) 1120 to move between the first and second positions. The position(s) of the depressible section 1116 and the penetrating member(s) 1120 may depend on the position of the elongate member 1140 with respect to the sheath 1110.

In some embodiments, the elongate member 1140 may include a first (distal) end 1142, an opposing second (proximal end) 1144, and a length therebetween. In some embodiments, the elongate member 1140 may be concentric partially or entirely along its length. In other embodiments, the elongate member 1140 may have a different shape.

In some embodiments, the elongate member 1140 may be partially or completely solid. In other embodiments, the elongate member 1140 may be partially or completely hollow, for example to provide a channel through which a therapeutic agent can flow.

The elongate member 1140 may be made of any known biocompatible material. The material may be rigid and/or flexible. In some embodiments, the materials may include but are not limited to one or more the following materials: metallic alloys, shape memory alloy (e.g., Nitinol), thermoplastic elastomer, urethane, polymer, polypropylene, plastic, ethylene chlorotrifluoroethylene (ECTFE), polyterafluoroethylene (PTFE), fluorinated ethylene propylene copolymer (FEP), nylon, resin, polyurethane, combinations thereof, and the like.

In some embodiments, the elongate member 1140 may be rigid in at least one direction. In some embodiments, the elongate member 1140 may be radially rigid. In other embodiments, the elongate member 1140 may be entirely or partially flexible in at least one direction. In some embodiments, a portion of the elongate member 1140 along its length may be flexible. In some embodiments, the elongate member 1140 may include an element that is configured to be more readily pulled than pushed; i.e., the elongate member 1140 may be configured to transfer force by retraction rather than by advancing. In some embodiments, the elongate member 1140 can include a wire. In some embodiments, the elongate member 1140 can include one or more fibers or filaments, such as a cord, string, or yarn that may be made of metal or aramid, for example.

In some embodiments, the elongate member 1140 may have a diameter that varies along its length. The diameters may be configured to control the movement of the depressible section 1116 and/or penetrating member(s) 1120 of the sheath 1110. The diameters of the elongate member 140 may depend on the location of the depressible section and/or configuration of the sheath 1110.

In some embodiments, at least one of the diameters of the elongate member 1140 may be configured to support the depressible section 1116 to maintain the penetrating member(s) 1120 in the aligned position when positioned adjacent to the depressible section 1116. At least another one of the diameters may be configured to support the depressible section 1116 to maintain the penetrating member 1120 in a protruded position when positioned adjacent to a portion of the depressible section 1116.

In other embodiments, the elongate member 1140 may have the same diameter along its length.

In some embodiments, the elongate member 1140 may include more than one section. The elongate member 1140 may include any number of sections. In some embodiments, the elongate member 1140 may include at least a first section 1152, a second section 1154, and a third section 1158. In some embodiments, the elongate member 1140 may include more or less sections.

In some embodiments, at least a portion of the first section 1152 may be configured to support the depressible section 1116 to maintain the penetrating member(s) 1120 in the aligned position when positioned adjacent to the depressible section 1116. The first section may have a first diameter along partially or entirely along the length of the first section 1152. The first diameter may substantially correspond to the inner diameter of the sheath 1110. The first diameter, however, may be slightly smaller than the inner diameter of the sheath 1110 to allow movement of the elongate member 1140 within the inner channel 1102. In some embodiments, the first diameter may be configured to substantially prevent a therapeutic agent and/or a medical fluid from flowing through the inner channel 1102.

In some embodiments, at least a portion of the second section 1154 may be configured to support the depressible section 1116 in the depressed position to maintain the penetrating member 1120 in the protruded position when positioned adjacent to a portion of the depressible section 1116. The second section 1154 may have a second diameter that is less than the first diameter. In some embodiments, the second section 1154 may have a tapered diameter partially along the length and/or circumference of the second section 1154. The tapering of the diameter may be based on the length and shape of the penetrating member 1120 and/or desired delivery of a therapeutic agent. The tapered diameter may be configured so that the elongate member 1140 may be configured to support a portion of the depressible section 1116. In some embodiments, the tapered diameter may be configured to restrain the depression of the depressible section 1116.

In some embodiments, the elongate member 1140 may include at least one tapered surface configured to support the depressible section 1116. In some embodiments, the tapered surface may be configured to control the delivery of a therapeutic agent from the delivery device 1100.

Figure 19:
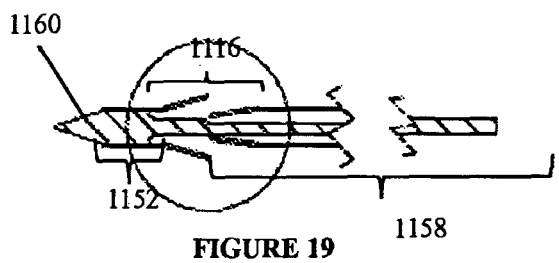
FIG. 19 shows a partial cross-sectional view of the delivery device taken along the line 19-19 of FIG. 18.
Figure 20:
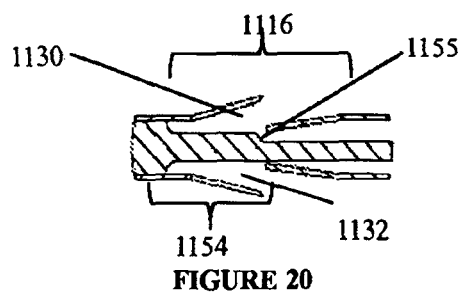
FIG. 20 shows an enlarged view of the delivery device of FIG. 19.
Figures 21, 22:
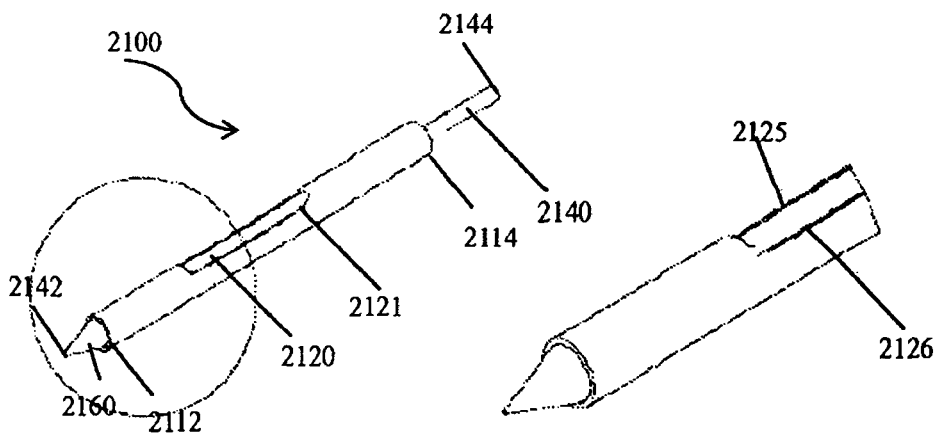
FIG. 21 shows a delivery device according to embodiments.
FIG. 22 shows an enlarged view of the delivery device of FIG. 21.
Figure 23:
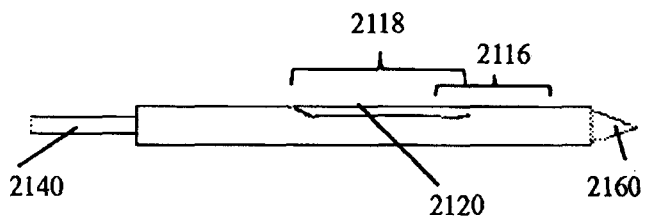
FIG. 23 shows a side view of the delivery device of FIG. 21.
Figure 24:
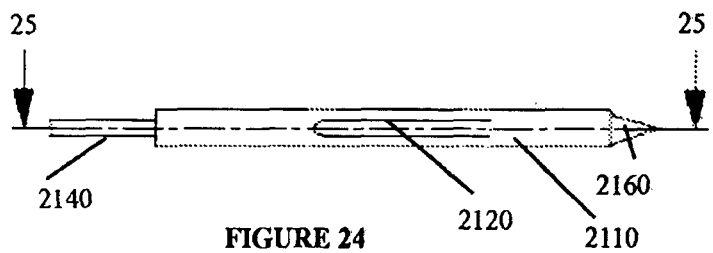
FIG. 24 shows a top view of the delivery device of FIG. 21.

As shown in FIGS. 19 and 20, the second section 1154 may include a tapered surface 1155 on one side of the elongate member 1140. The tapered surface 1155 may allow the opening 1132 to be larger than the opening 1134 that does not include tapering, thereby the opening 1132 being configured to deliver more therapeutic agent than opening 1134. In other embodiments, the second section 1154 may include another tapered surface that is symmetric or asymmetric to the tapered surface 1155 disposed on the other side.

In some embodiments, the third section 1158 may have a third diameter that is less than the first diameter and the second diameter. The third section 1158 may be parallel to the first section 1154. The third diameter may be configured to allow flow of a therapeutic agent and/or another medical fluid through the inner channel 1102 of the sheath 1110.

In some embodiments, the elongate member 1140 may include at least one puncture member 1160 configured to penetrate the treatment site. In some embodiments, the puncture member 1160 may be configured to separate tissue rather than core the tissue at the treatment site. In other embodiments, the puncture member 1160 may be configured to partially or entirely core tissue at the treatment site.

In some embodiments, a puncture member 1160 may be disposed at the first end 1142. In other embodiments, the elongate member 1140 may include additional puncture member(s) disposed along its length. For example, the elongate member 1140 may include one, two, three, or more than three puncture members along its length. The puncture members may have the same or different shape and/or configuration.

In some embodiments, the puncture member 1160 may include a sharp tip or blunt tip. In some embodiments, the sharpness of the puncture member 1160 may depend on the tissue of the treatment site.

In some embodiments, the puncture member 1160 may have a conical shape as shown in FIGS. 11 through 20. In other embodiments, the puncture member 1160 may have a different shape. In some embodiments, the puncture member 1160 may have single faceted, multi-faceted shape, conical shape, or a combination thereof. The shape of the puncture member 1160 may depend on any one of the sheath, the tissue type, location, and access path of the treatment site.

In operation, the clinician may position the delivery device 1100 at a treatment site intended to be treated, such as a diseased tissue. The delivery device 1100 may be positioned at the treatment site while the depressible section 1116 is in a first or aligned position, as shown in FIGS. 11 through 15, with the penetrating members 1120 retracted. Working from the proximal end 1114 of the delivery device 1100, the clinician may fix the sheath 1110 in position and move the elongate member 1140 forward toward the treatment site so that a portion of the elongate member 1140 extends from the distal end 1112, as shown in FIGS. 16 through 20. While the elongate member 1140 is being moved towards the distal end 1112 of the delivery device 1100, the depressible section 1116 may move into the second or depressed position thereby causing the penetrating member(s) 1120 to deploy, moving into the second or protruded position to penetrate or cut tissue at the treatment site. In the second position, the penetrating member(s) 1120 and/or elongate member 1140 may form channels at the treatment site. If additional channels are desired, the clinician may retract the elongate member 1140 toward the proximal end 1114 so that the depressible section 1116 moves into the aligned position and then may rotate the sheath 1110, for example, 90 degrees, and repeat the process to penetrate the tissue at different locations at the treatment site. After a desired number of channels are formed by the penetrating member(s) 1120, the clinician may cause the delivery device 100 to deliver a therapeutic agent. The therapeutic agent may be delivered through the openings 1132 and 1134. Additionally, the clinician may rotate the sheath 1110 (or the entire delivery device 1100) with the penetrating member(s) 1120 deployed in order to create a circumscribing cut, for example, to create a surface of revolution with the tissue.

Because the penetrating member(s) 1120 are configured to form at least pressure channel(s), the generated pressure at the treatment site may cause the cuts in the tissue to push tissue flaps together when the elongate member 1140 is retracted after the agent is delivered, thereby preventing the agent from leaking along the path of the delivery device 1100 as it is removed.

Figure 42A:
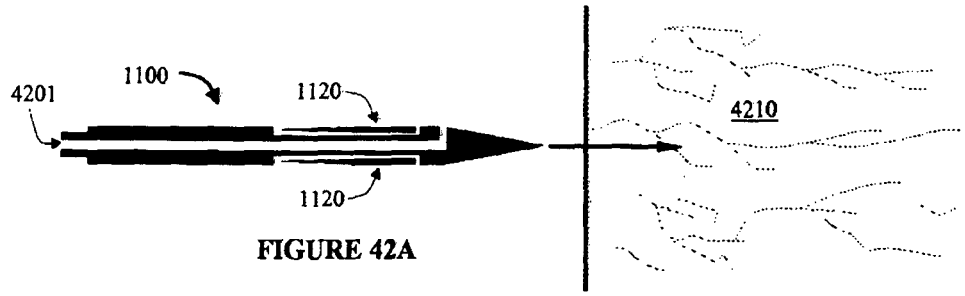
FIGS. 42A-42N show delivery device operation according to embodiments.
Figure 42B:
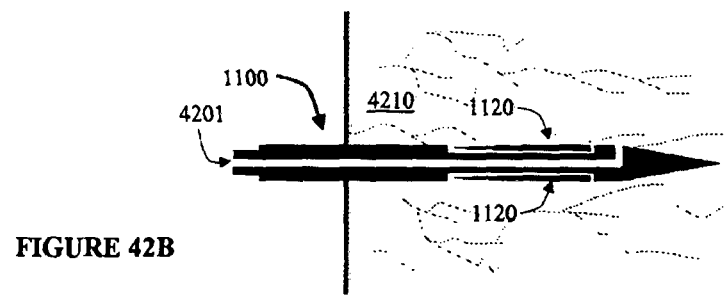
Figure 42C:
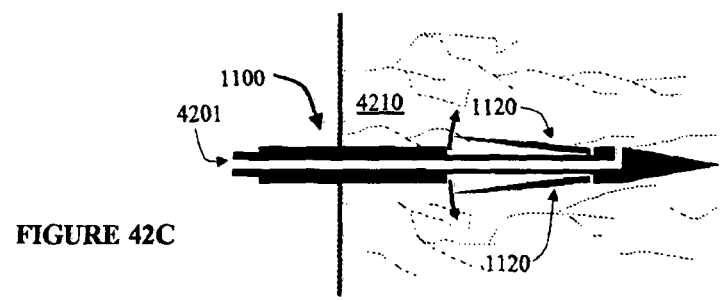
Figure 42D:
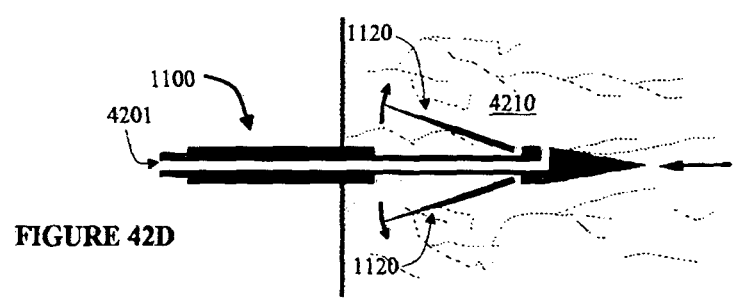
Figure 42E:
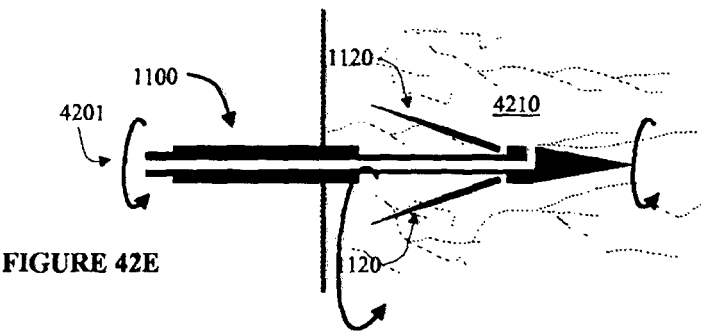
Figure 42F:
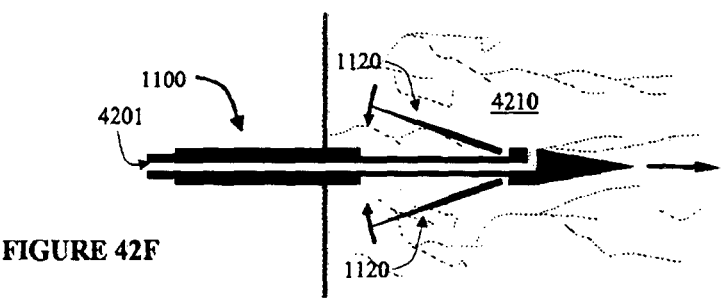
Figure 42G:
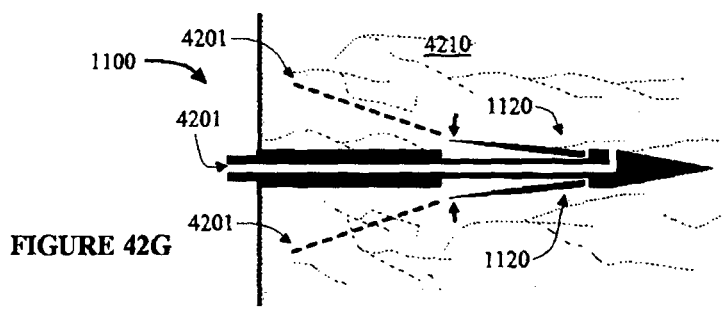
Figure 42H:
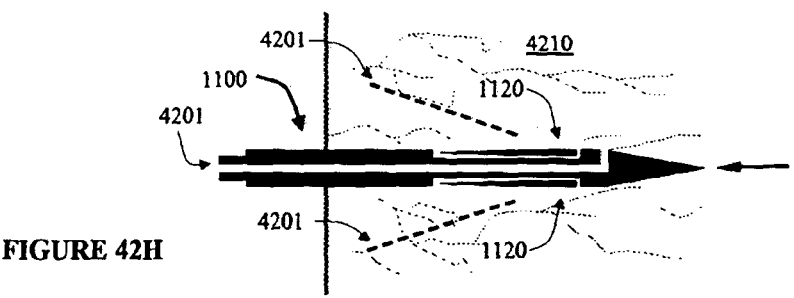
Figure 42I:
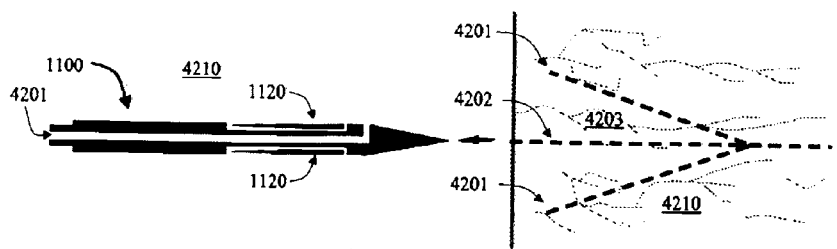
Figure 42J:
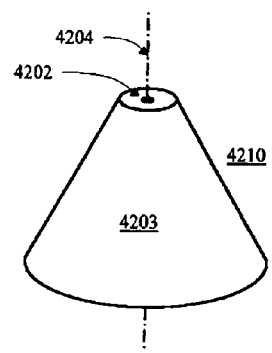
Figure 42K:
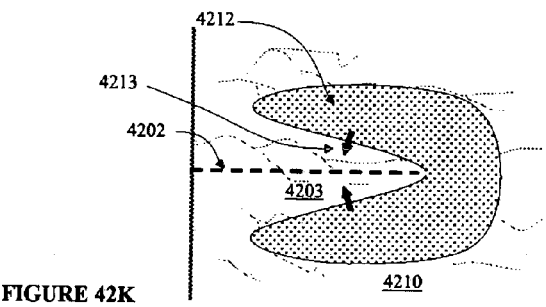
Figure 42L:
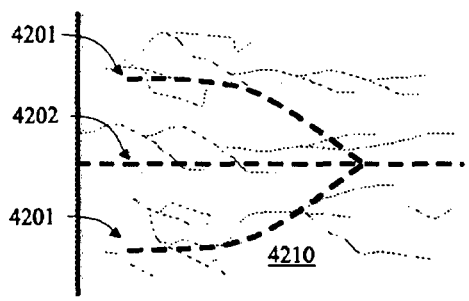
Figure 42M:
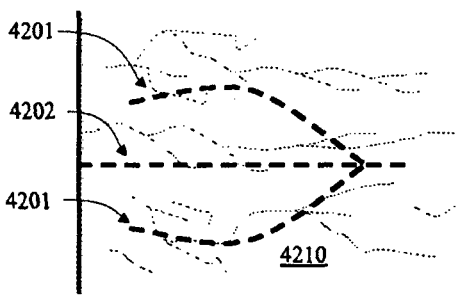
Figure 42N:
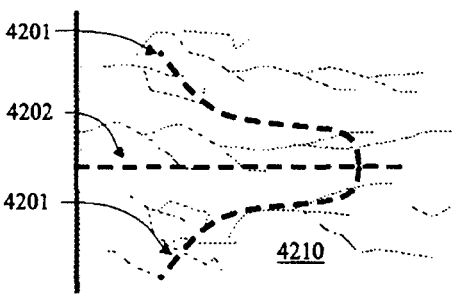

FIGS. 42A-42N show operation of delivery devices configured in correspondence to the delivery device 1100 illustrated in FIGS. 11-20 and thus will be referred to in the following discussion as the delivery device 1100, without limitation and without suggesting that operations or processes are limited to any one illustrated embodiment.

FIG. 42A shows the delivery device 1100 in preparation for puncturing tissue 4210 to deliver a therapeutic agent 4212 (shown in FIG. 42K), such as therapeutic cells injected through a catheter into the myocardium of a living human heart during a medical procedure to treat ischemic damage associated with an infarct event. In the illustrated embodiment, the delivery device 1100 includes a centrally disposed lumen 4201 through which the therapeutic agent 4212 flows for emission through a side port that is located on the proximal side of the leading tip of the delivery device 1100. In preparation for puncturing the tissue 4210, the penetrating members 1120 of the delivery device 1100 are in a retracted position.

FIG. 42B shows the delivery device 1100 advanced, for example having punctured the tissue 4210. During a medical procedure, the operation shown in FIG. 42B may temporally follow the operation shown in FIG. 42A.

FIG. 42C shows the penetrating members 1120 of the delivery device 1100 in a partially deployed state, whereby the penetrating members 1120 are beginning to deploy. In this state, the tips of the penetrating members 1120 are oriented to catch the tissue 4210 and are beginning to engage and penetrate the tissue 4210. Thus, the penetrating members 1120 have opened sufficiently so that the tips of the penetrating members 1120 are in a penetrating position. The delivery device 1100 may synchronously retract and open its penetrating members 1120. During a medical procedure, the operation shown in FIG. 42C may temporally follow the operation shown in FIG. 42B.

FIG. 42D shows the delivery device 1100 retracted relative to the position of the device shown in FIG. 42C. Here, the penetrating members 1120 are fully deployed, open and have fully penetrated the tissue 4210. As the delivery device 1100 is retracted, the penetrating members 1120 fully engage the tissue 4210 and swing open. In some embodiments, the tips of the penetrating members 1120 catch the tissue 4210 during device retraction, and the tissue urges the penetrating members 1120 further open as the penetrating members 1120 penetrate the tissue 4210. Accordingly, each penetrating member 1120 creates a respective channel in the tissue 4210. During a medical procedure, the operation shown in FIG. 42D may temporally follow the operation shown in FIG. 42C.

FIG. 42E shows the delivery device 1100 rotating around its longitudinal axis, causing the opened penetrating members 1120 to revolve circumferentially with respect to that axis. In some embodiments, the penetrating members 1120 include sharp edges so as to cut the tissue 4210 as they revolve. In some embodiments, the penetrating members 1120 revolve while the main body of the delivery device 1100 remains stationary; for example the penetrating members 1120 can be driven to rotate by a spring that is released by the clinician or automatically, under machine control. In many applications, revolving the penetrating members 1120 to cut a path circumscribing the delivery device 1100 is optional, as the penetrating members 1120 may form sufficient channels to impede backflow of the therapeutic agent 4212 without revolution. During a medical procedure, the operation shown in FIG. 42E, if executed, may temporally follow the operation shown in FIG. 42D.

FIG. 42F shows the delivery device 1100 moving forward, further or deeper into the tissue 4210, as the penetrating members 1120 close. Moving the delivery device 1100 forward as the penetrating members 1120 close helps maintain integrity of the tissue 4210 that is between the delivery device 1100 and the tips of the extended penetrating members 1120. The delivery device 1100 may synchronously advance, i.e. move forward, and close its penetrating members 1120. During a medical procedure, the operation shown in FIG. 42F may temporally follow the operation shown in FIG. 42D and FIG. 42E (if the operation shown in FIG. 42E is executed).

FIG. 42G shows the delivery device 1100 advanced, i.e. moved forward, and the penetrating members 1120 substantially closed. Accordingly, the penetrating members 1120 have formed a channel (or channels) 4201 in intact tissue 4210. At this stage, the therapeutic agent 4212 can be delivered through the lumen 4201, as will be discussed in further detail below with reference to FIG. 42K. During a medical procedure, the operation shown in FIG. 42G may temporally follow the operation shown in FIG. 42F.

FIG. 42H shows the delivery device 1100 retracting from the tissue 4210 with the penetrating members 1120 closed. During a medical procedure, the operation shown in FIG. 42H may temporally follow the operation shown in FIG. 42G.

FIG. 42I shows the delivery device 1100 retracted from the tissue 4210. During a medical procedure, the operation shown in FIG. 42I may temporally follow the operation shown in FIG. 42H. The delivery device 4210 has formed a main channel 4202 and one or more secondary channels 4201. If the penetrating members 1120 revolved fully around the longitudinal axis 4204 of the delivery device 1100, as discussed above with reference to FIG. 42E, the penetrating members 1120 may have formed a surface of revolution. For example, two penetrating members 1120 rotating 180 degrees may form a conical or tapered surface 4203 within the tissue, as shown in FIG. 42J. As another example, a single penetrating member rotating 120 degrees would form a surface of revolution about an axis 4204 that stops short of full closure.

FIG. 42K shows the therapeutic agent 4212 delivered via the main channel 4202. In some embodiments, the therapeutic agent 4212 is delivered while the delivery device 1100 is inserted in the tissue, such as in a state shown in FIG. 42G as discussed above, or between the states of FIGS. 42G and 42H, or as the delivery device 1100 is retracted as shown in FIG. 42H, for example. In some embodiments, the therapeutic agent 4212 is delivered after the delivery device 1100 is extracted, for example via inserting a tube or needle into the main channel 4202. The therapeutic agent 4202 may also be forced to flow into the main channel 4202 by pressure applied external to the tissue 4210, without inserting any member into the main channel 4202. For example, a seal may be created at the proximal end of the main channel 4202, and the therapeutic agent 4212 driven into the main channel 4202 under fluid/hydraulic pressure. Whether delivered through the delivery device 1100 or some other appropriate means, the therapeutic agent 4212 may move into the secondary channel or channels 4201 under pressure. The pressure applies force 4213 to the intact tissue located between the secondary channel 4201 and the main channel 4202 and that tissue transfers force 4213 to the main channel 4202. The force 4213 urges the main channel 4202 closed, thereby impeding or checking backflow of the therapeutic agent 4212 through the main channel 4202. Accordingly, retention of the therapeutic agent 4202 is enhanced, providing the main channel 4202 an opportunity to seal fully and permanently. In some embodiments, when the myocardium contracts as a human heart beats, the pressure of myocardial contraction elevates pressure of the pocket of therapeutic agent 4212, thereby further compressing the main channel 4202 closed.

FIGS. 42L, 42M, and 42N show additional examples of channel geometries that the delivery device 1100, according to embodiments, can be configured to create. As shown in FIG. 42L, the secondary channels 4201 can be curved such that throughout length of the secondary channel 4201, distance from the main channel 4202 increases. As shown in FIG. 42M, the secondary channels 4201 can be curved like a football, such that through length of the secondary channel 4201, distance from the main channel 4202 increases, peaks, and then decreases. As shown in FIG. 42N, the secondary channels 4201 can be curved like a tulip. Channel forms such as those depicted in FIGS. 42L, 42M, and 42N can be formed using penetrating members 1120 that are shaped into a desired geometry. In some embodiments, each penetrating member 1120 is at least as long as the diameter of the delivery device 1100. In some embodiments, each penetrating member 1120 is at least two, or three, or four, or five times as long as the diameter of the delivery device.

FIGS. 21 through 32 show a delivery device 2100 according to different embodiments. A delivery device 2100 may include a sheath 2110. The delivery device 2100 may also include an elongate member 2140 configured to be movable with respect to the sheath 2110.

In some embodiments, the sheath 2110 may include a first (distal) end 2112, an opposing second (proximal) end 2114, and a length therebetween. The sheath 2110 may include an inner channel or lumen 2102 that extends along its length between the first end 2112 and the second end 2114. In some embodiments, the sheath 2110 may include an opening disposed at each of the ends.

In some embodiments, the sheath 2110 may have a substantially uniform cylindrical shape along at least a portion of its length. In some embodiments, the sheath 2110 may have substantially the same outer diameter along its length. In other embodiments, the sheath 2110 may have different shapes or diameters along its length. In some embodiments, the sheath 2110 may have different inner diameters along the length.

In some embodiments, the sheath 2110 may include a plurality of sections. The sections may be made of the same or different materials. In some embodiments, the sections may be made of a same material but at least one of the sections may have different properties, such as, elastic properties. In some embodiments, one or more of the sections may be made of a flexible material.

The materials may include but are not limited to one or more the following materials:

metallic alloys, shape memory alloy (e.g., Nitinol), thermoplastic elastomer, urethane, polymer, polypropylene, plastic, ethylene chlorotrifluoroethylene (ECTFE), polytetrafluoroethylene (PTFE), fluorinated ethylene propylene copolymer (FEP), nylon, resin, polyurethane, combinations thereof, and the like.

In some embodiments, one of the sections the sheath 2110 may include at least one reversibly depressible or collapsible (hereinafter referred to as "depressible" and also referred to as a "first") section 2116 disposed along its length. In some embodiments, the sheath 2110 may include more than one depressible section 2116 disposed along its length. The depressible section 2116 may be configured to move between a first (aligned) position as shown in FIGS. 21 through 26 and a second (depressed) position as shown in FIGS. 27 through 32. The aligned position may include when the depressible section 2116 is substantially aligned with the outer diameter, for example, as shown in FIGS. 21 through 26. The depressed position may include when the depressible section 2116 is depressed into the inner channel 2102, for example, as shown in FIGS. 27 through 32.

In some embodiments, the movement of the depressible section 2116 from the aligned and depressed positions may be based on the movement or position of an elongate member with respect to the sheath 2110. The depressible section 2116 may be configured to depress or collapse from the outer or first diameter into the inner channel 2102 when not supported, for example, by the elongate member. The movement of the depressible section 2116 between the two positions may be strained induced.

The depressible section 2116 may be disposed between the first end 2112 and the second end 2114 of the sheath. In some embodiments, the depressible section 2116 may be disposed closer to the first end 2112 than the second end 2114. For example, the depressible section 2116 may be disposed about ⅓ or ¼ along the length from the first end. However, it will be understood that the depressible section 1116 is not limited to this location. In other embodiments, the depressible section 2116 may be disposed at other positions along the length of the sheath 2110.

In some embodiments, one of the sections of the sheath 2110 may include an indented (also referred to as a "second") section 2118 disposed along its length. The indented section 2118 may be disposed on at least one side of the sheath 2110. In some embodiments, the indented section 2118 may be disposed adjacent to the depressible section 2116 along the length of the sheath 2110. The indented section 2118 may be disposed between the depressible section 2116 and the second end 2114.

In some embodiments, the indented section 2118 may include a tapered surface 2119. In other embodiments, the indented section 2118 may not include the tapered surface 2119 or include alternatively or additionally, a different surface.

In some embodiments, the sheath 2110 may include at least one penetrating member 2120 disposed along its length. The at least one penetrating member 2120 may be configured to reversibly move between a first (aligned) or closed position as shown in FIGS. 21 through 26 and a second (protruded) or opened position as shown in FIGS. 27 through 32.

In the aligned position, the penetrating member 2120 may be substantially aligned with the outer diameter of the sheath 2110. As shown in FIGS. 21 through 26, the penetrating member 2120 may be configured to rest within the indented section 2118 when in the aligned position. The indented section 2118 may be configured so that the penetrating member 2120, when in the aligned position, may be substantially parallel with the outer diameter of the sheath 2120. For example, the length and depth of the indented section 2118 may depend on the length and diameter/width of the penetrating member 2120.

In the protruded position, the penetrating member 2120 may protrude at an angle from the outer diameter of the sheath 2110. The penetrating member 2120 may be configured to protrude toward the first end 2112 or the second end 2114. The penetrating member 2120 may be configured to protrude from the sheath 2110 at any angle. In some embodiments, the angle of protrusion may be about 45 degrees or less. In other embodiments, the angle of protrusion may be more than 45 degrees.

Configuring the penetrating member 2120 to be pointed proximally when deployed can facilitate therapeutic agent retention. In this configuration, the delivered therapeutic agent can form a pocket that applies lateral pressure to the primary track or channel in the tissue that remains after the delivery device 2100 is removed. Accordingly, the delivered therapeutic agent can pinch the delivery channel closed so that backflow is checked.

In some embodiments, the movement of the penetrating member 2120 may depend on the position or state of the depressible section 2116. For example, when the depressible section 2116 is in the first or aligned position, the penetrating member 2120 may be in the first or aligned position as shown in FIGS. 21 through 26. The penetrating member 2120 may be in the second or protruded position as shown in FIGS. 27 through 32 when the depressible section 2116 is in the second or depressed position.

In some embodiments, as shown in FIGS. 11 through 20, the sheath 2110 may include one penetrating member 2120. As shown in FIGS. 11 through 20, the sheath 110 may include more than one penetrating member disposed at the same or different positions as the penetrating member 2120.

In some embodiments, the penetrating member 2120 may be disposed at or adjacent to the depressible section 2116 and/or the indented section 2118. In other embodiments, the penetrating member 2120 may be disposed at other positions along the length of the sheath 2110. For example, the location of the penetrating member 2120 is not limited to the position with respect to the sheath 2110 as shown in FIGS. 21 through 32. The penetrating member 2120 and the depressible section 2116 may be disposed at other location(s) along the length of the sheath 2110.

In some embodiments, the penetrating member 2120 may include at least one puncture member 2121 configured to penetrate into the treatment site to form a channel in tissue at the treatment site when the penetrating member 2120 is in a protruded position, as shown in FIGS. 27 through 32. In some embodiments, the puncture member 2121 may be configured to separate tissue rather than core the tissue at the treatment site. In other embodiments, the puncture member 2121 may be configured to partially or entirely core tissue at the treatment site.

In some embodiments, the puncture member 2121 may include a puncture tip 2123. In some embodiments, the puncture tip 2123 may be beveled. In other embodiments, the puncture tip 2123 may have a different shape. In some embodiments, the puncture tip 2123 may depend on the shape of the tapered surface 2119 of the indented section 2118. The puncture tip 2123 may be configured to be disposed adjacent to the tapered surface 2119 when the penetrating member 2120 is in the aligned position.

In some embodiments, the puncture member 2121 may additionally or alternatively include at least one puncture edge. In some embodiments, the puncture member 2121 may include two puncture edges 2125 and 2126.

In some embodiments, the penetrating member 2120 may have an elongated shape, for example like a needle, as shown in FIGS. 21 through 32. In some embodiments, the length of the penetrating member 2120 may depend on and/or based on the length of the indentation section 2118. In other embodiments, the penetrating member 2120 may have a different shape. In some embodiments, the penetrating member 2120 may be disposed so that the penetrating member 2120 protrudes at an angle from the outer diameter toward the second end 2114 when in the protruded or open position, as shown in FIGS. 27 through 32. In other embodiments, the penetrating member 2120 may be so that the penetrating member 2120 protrudes at an angle from the outer diameter toward the first end 2112 when in the protruded or open position.

In some embodiments, the penetrating member 2120 may be hollow. In some embodiments, the penetrating member may include an inner channel or lumen 2132 along its length. The channel 2132 may fluidly communicate with the inner channel 2102 of the sheath 2110, for example with the therapeutic agent delivered by flowing through the penetrating member 2120.

In some embodiments, the sheath 2110 may include at least one opening 2130 disposed along its length. In some embodiments, the at least one opening 2130 may be configured to deliver a therapeutic agent, for example, when the penetrating member 2120 is in the protruded or open position. In some embodiments, the opening 2130 may be disposed at the end of the penetrating member 2120. The opening may be fluidly connected to the inner channel 2102 of the sheath 2110 through the inner channel 2132.

In some embodiments, the sheath 2110 may include a coating on the outer surface to aid the placement of the delivery device 2100. For example, the outer surface may be treated with active agents to prevent platelet adhesion or aggregation and blood clot formation, such as an anticoagulant coating; a lubricant, such as a water-based, water-soluble lubricant; other materials, such as radiopaque coating material; or a combination thereof.

In some embodiments, the elongate member 2140 may be configured to move with respect to the sheath 2110. The elongate member 2140 may be configured to cause the depressible section 2116 and/or the penetrating member 2120 to move between the first and second positions. The position(s) of the depressible section 2116 and the penetrating member 2120 may depend on the position of the elongate member 2140 with respect to the sheath 2110.

In some embodiments, the elongate member 2140 may include a first (distal) end 2142, an opposing second (proximal end) 2144, and a length therebetween. In some embodiments, the elongate member 2140 may be concentric partially or entirely along its length. In other embodiments, the elongate member 2140 may have a different shape.

In some embodiments, the elongate member 2140 may be partially or completely solid. In other embodiments, the elongate member 2140 may be partially or completely hollow.

The elongate member 2140 may be made of any known biocompatible material. The material may be rigid and/or flexible. In some embodiments, the materials may include but are not limited to one or more the following materials: metallic alloys, shape memory alloy (e.g., Nitinol), thermoplastic elastomer, urethane, polymer, polypropylene, plastic, ethylene chlorotrifluoroethylene (ECTFE), polyterafluoroethylene (PTFE), fluorinated ethylene propylene copolymer (FEP), nylon, resin, polyurethane, combinations thereof, and the like.

In some embodiments, the elongate member 2140 may be rigid in at least one direction. In some embodiments, the elongate member 2140 may be radially rigid. In other embodiments, the elongate member 2140 may be entirely or partially flexible in at least one direction. In some embodiments, a portion of the elongate member 2140 along its length may be flexible. As discussed above with reference to other embodiments, the elongate member 2140 may include fibers or filaments and may transfer force and/or energy via tensioning rather than thrusting or pushing.

In some embodiments, the elongate member 2140 may have a diameter that varies along its length. The diameters may be configured to control the movement of the depressible section 2116 and/or penetrating member(s) 2120 of the sheath 2110. The diameters of the elongate member 2140 may depend on the location of the depressible section and/or configuration of the sheath 2110.

In some embodiments, at least one of the diameters of the elongate member 2140 may be configured to support the depressible section 2116 to maintain the penetrating member(s) 2120 in the aligned position when positioned adjacent to the depressible section 2116. At least another one of the diameters may be configured to support the depressible section 2116 to maintain the penetrating member 2120 in a protruded position when positioned adjacent to a portion of the depressible section 2116.

In other embodiments, the elongate member 2140 may have the same diameter along its length.

In some embodiments, the elongate member 2140 may include more than one section. The elongate member 2140 may include any number of sections. In some embodiments, the elongate member 2140 may include at least a first section 2152, a second section 2154, and a third section 2158. In some embodiments, the elongate member 2140 may include more or less sections.

In some embodiments, at least a portion of the first section 2152 may be configured to support the depressible section 2116 to maintain the penetrating member 2120 in the aligned position when positioned adjacent to the depressible section 2116. The first section 2152 may have a first diameter along partially or entirely along the length of the first section 2152. The first diameter may substantially correspond to the inner diameter of the sheath 2110. The first diameter, however, may be slightly smaller than the inner diameter of the sheath 2110 to allow movement of the elongate member 2140 within the inner channel 2102. In some embodiments, the first diameter may be configured to substantially prevent a therapeutic agent and/or a medical fluid from flowing through the inner channel 2102.

In some embodiments, at least a portion of the second section 2154 may be configured to support the depressible section 2116 in the depressed position to maintain the penetrating member 2120 in the protruded position when positioned adjacent to a portion of the depressible section 2116. The second section 2154 may have a second diameter that is less than the first diameter. In some embodiments, the second section 2154 may have a tapered diameter partially along the length and/or circumference of the second section 2154. The tapering of the diameter may be based on the length and shape of the penetrating member 2120 and/or desired delivery of a therapeutic agent. The tapered diameter may be configured so that the elongate member 2140 may be configured to support a portion of the depressible section 2116. In some embodiments, the tapered diameter may be configured to restrain the depression of the depressible section 2116.

In some embodiments, the elongate member 2140 may include at least one tapered surface configured to support the depressible section 2116. In some embodiments, the tapered surface may be configured to control the delivery of a therapeutic agent from the delivery device 2100.

Figure 25:
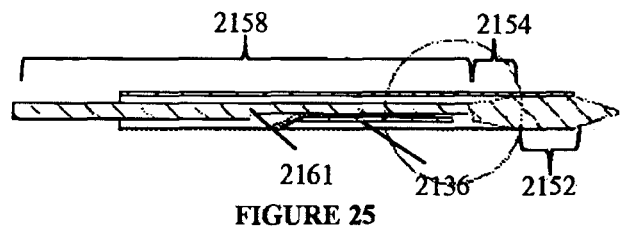
FIG. 25 shows a cross-sectional view of the delivery device taken along the line 25-25 of FIG. 24.
Figure 26:
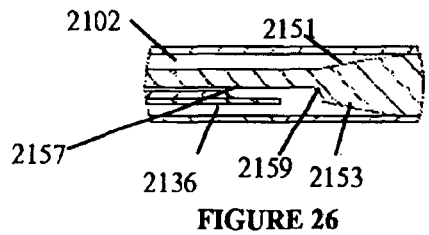
FIG. 26 shows an enlarged view of the delivery device of FIG. 25.

As shown in FIGS. 25 and 26, the second section 2154 may include two tapered surfaces 2153 and 2159 on the elongate member 2140. The tapered surfaces 2153 and 2159 may be substantially symmetric.

In some embodiments, the third section 2158 may have a third diameter that is less than the first diameter and the second diameter. The third section 2158 may be parallel to the first section 2154. The third diameter may be configured to allow flow of a therapeutic agent and/or another medical fluid through the inner channel 2102 of the sheath 2110.

In some embodiments, the elongate member 2140 may include at least one track 2157 disposed at least partially along its length configured to at least control the movement of the elongate member 2140 and/or penetrating member 2120 with respect to the sheath 2110. In some embodiments, the track 2157 may also be configured to substantially prevent the delivery of the therapeutic agent and/or fluid through the opening 2130 when the penetrating member 2120 is in the deployed position. In some embodiments, the track 2157 may be a groove or indentation provided along the length of the elongate member 2140.

As shown in FIGS. 25 and 26, the track 2157 may be disposed at least on one side of the elongate member 2140. The track 2157 may be disposed on the same side as the penetrating member 2120. In some embodiments, the track 2157 may be disposed adjacent to the second section 2154. In other embodiments, the track 2157 may be disposed additionally or alternatively at other locations of the elongate member 2140, for example, on the other side and/or or at a different location along the length of the elongate member 2140.

In some embodiments, the diameter of the elongate member 2140 along the length of the track 2157 may be less than the third diameter. In some embodiments, the depth, diameter, and/or length of the track 2157 of the elongate member 2140 may depend on the dimensions of the penetrating member 2120.

In some embodiments, the track 2157 may be configured to restrain the movement of the elongate member 2140 with respect to the sheath 2110. In some embodiments, the track 2157 may include tapered surfaces 2159 and 2161 on each end. The tapered surfaces 2159 and 2161 may have dimensions that substantially correspond to the depth of the penetrating member 2120 and the tapered surface 2119 of the sheath 2110, respectively. The tapered surface 2159 may be configured to restrain the distal movement of the elongate member 2140, i.e., the movement of the elongate member 2140 towards the distal or first end 2112 of the sheath 2110. The tapered surface 2161 may be configured to restrain the proximal movement of the elongate member 2140, i.e., the movement of the elongate member 2140 towards the proximal or second end 2114 of the sheath 2110.

In some embodiments, the elongate member 2140 may include at least one puncture member 2160 configured to penetrate the treatment site. In some embodiments, the puncture member 2160 may be configured to separate tissue rather than core the tissue at the treatment site. In other embodiments, the puncture member 2160 may be configured to partially or entirely core tissue at the treatment site.

In some embodiments, a puncture member 2160 may be disposed at the first end 2142. In other embodiments, the elongate member 2140 may include additional puncture member(s) disposed along its length. For example, the elongate member 2140 may include one, two, three, or more than three puncture members along its length. The puncture members may have the same or different shape and/or configuration.

In some embodiments, the puncture member 2160 may include a sharp tip or a blunt tip. In some embodiments, the sharpness of the puncture member 2160 may depend on the tissue of the treatment site.

In some embodiments, the puncture member 2160 may have a conical shape as shown in FIGS. 21 through 32. In other embodiments, the puncture member 2160 may have a different shape. In some embodiments, the puncture member 2160 may have single faceted, multi-faceted shape, conical shape, or chiseled or beveled shape, or a combination thereof. The shape of the puncture member 2160 may depend on any one of the sheath, tissue type, location, and access path of the treatment site.

Figure 38:
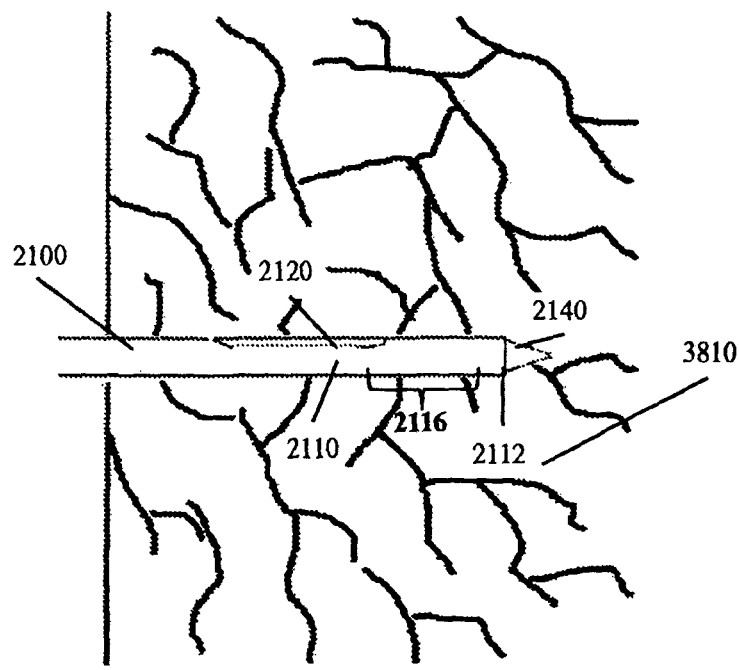
FIG. 38 shows an example of the delivery device of FIG. 21 in a state of operation.

An example of operation of the delivery device 2100 is shown in FIGS. 38 through 41. In operation, the clinician may position the delivery device 2100 at treatment site 3810 intended to be treated, such as a diseased tissue. The delivery device 2100 may be positioned at the treatment site 3810 while the depressible section 2116 is in a first or aligned position, as shown in FIG. 38. This may correspond to the position shown in FIGS. 21 through 26.

Figure 39:
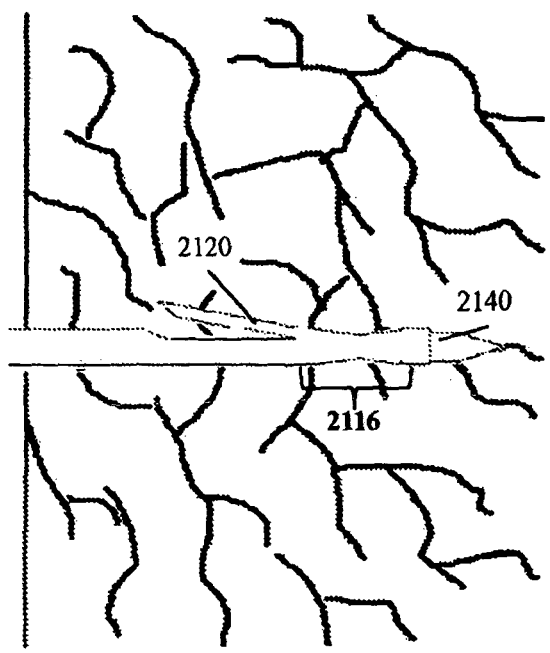
FIG. 39 shows the delivery device of FIG. 38 in a different state of operation.

Working from the proximal end 2114 of the delivery device 2100, the clinician may hold the sheath 2110 in a fixed position and move the elongate member 2140 forward toward the treatment site 3810 so that a portion of the elongate member 2140 extends from the distal end 2112, as shown in FIG. 39. This may correspond to the position shown in FIGS. 27 through 32. While the elongate member 2140 is being moved towards the distal end 2112 of the delivery device 2100, the depressible section 2116 moves into the second or depressed position thereby causing the penetrating member(s) 2120 to move into the second or protruded position to begin engaging tissue at the treatment site. As the penetrating member 2120 is deployed and extends, the point of the penetrating member 2120 may catch the tissue, and the clinician may slightly retract the delivery device 2100. As the delivery device 2100 is retracted, the penetrating member 2120 may swing to its fully open position. Retraction and opening can be synchronous. In this position, the point and opening 2130 of the penetrating member 2120 is separated from the main body of the delivery device by a section of intact tissue. Thus, the delivery device 2100 has created in the tissue a channel that extends into the tissue and that folds back on itself. That is, the resulting channel extends distally and then, in a corner or abrupt change in path, turns back and extends proximally. The section 4110 of the channel that extends distally and the section 4112 of the channel that extends proximally can form an acute angle, for example. In some embodiments, these two channel sections 4110 and 4112 may lie in a common plane or run alongside a common plane. In some embodiments, either or both of the two channel sections 4110 and 4112 may be substantially linear. In some embodiments, either or both channels 4110 and 4112 may be curved.

Figure 40:
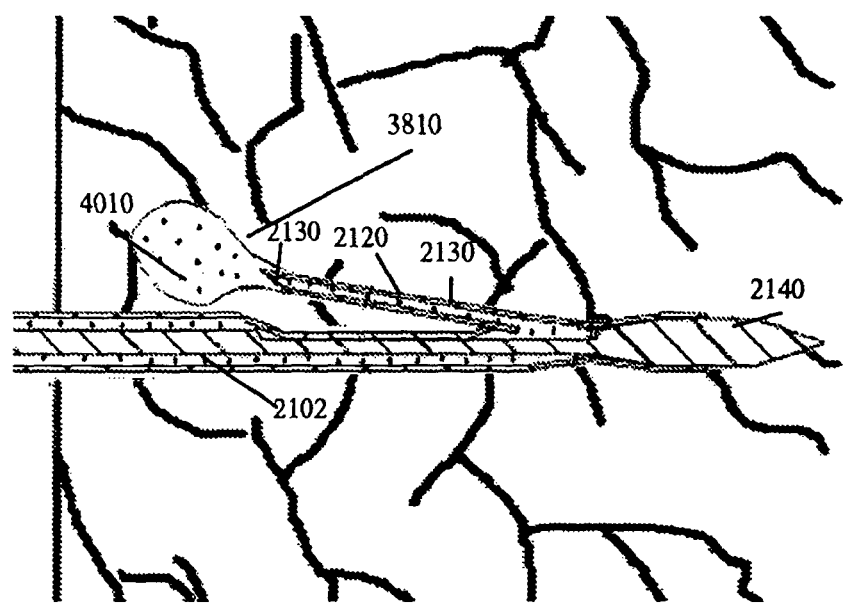
FIG. 40 shows the delivery device of FIG. 38 in a different state of operation.

Once the penetrating member 2120 is deployed, the clinician may cause the delivery device 2100 to deliver a therapeutic agent 4010. As shown in FIG. 40, the delivery device 2100 may be configured to deliver the agent through the opening 2130. The therapeutic agent 4010 may travel through the inner channel 2102 of the sheath to the inner channel 2136 of the penetrating member 2120 to exit the opening 2130 to the treatment site 3810.

In some embodiments, removal of the delivery device 2100 entails reversing the steps of device insertion and deployment of the penetrating member 2120. Thus, the penetrating member 2120 can fold down into the position shown in FIG. 38 as the clinician advances the delivery device 2100 forward, thereby keeping intact the tissue that is between the delivered therapeutic agent 4010 and the main delivery channel 4110. Once the penetrating member 2120 is retracted into the main body of the delivery device 2100, the clinician can extract the delivery device 2100.

Figure 41:
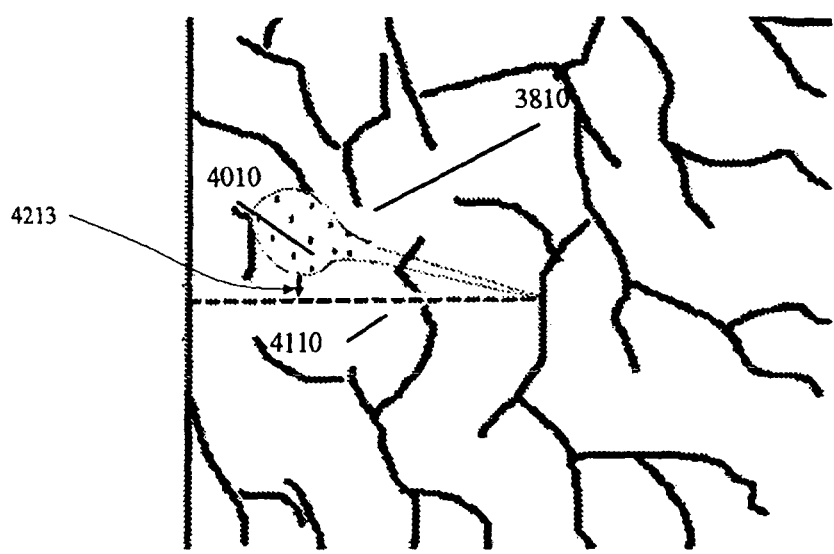
FIG. 41 shows the treatment site after the delivery of a therapeutic agent by the delivery device of FIG. 38.

As shown in FIG. 41, the delivered therapeutic agent 4010 applies lateral pressure 4213 to the main delivery channel 4110, effectively pinching the main delivery channel 4110 closed. Pressure of the delivered therapeutic agent 4010 transfers to the main deliver channel 4110 across the intact tissue that is between the delivered therapeutic agent 4010 and the main delivery channel, checking backflow or preventing leakage of the therapeutic agent through the main delivery channel 4110.

In some embodiments, the delivery device 2100 is configured to form a check valve in the tissue, such that the therapeutic agent 4010 flows into the treatment site 3810 more readily that it flows out of the treatment site 3810. In some embodiments, the pressure of the delivered therapeutic agent 4010 exceeds the cracking pressure of the check valve formed in the tissue.

In some embodiments, the delivery device 2100 may include a cutter located where the penetrating member 2120 connects to the main body of the delivery device 2100. For example, two foldable blades may be connected between the main body of the delivery device 2100 and the penetrating member 2120 in the area 2139 indicated on FIG. 32. One blade can span between one lateral side of the penetrating member 2120 and the main body of the delivery device 2100, while the other blade can span between the other lateral side of the penetrating member 2120 and the main body of the delivery device 2100. In some embodiments, the blades can be thin strips of metal having a sharp proximal edge, and the strips can be folded, accordion style, to that they are collapsible. In some embodiments, such strips can have a width that is about one-third or less the total length of the penetrating member 2120. In some embodiments, the blades can be thin wires that are able to cut tissue. When the penetrating member 2120 deploys as the clinician retracts the delivery device as discussed above, such blades may cut a flap into the tissue. When the therapeutic agent 4010 is delivered, the therapeutic agent 4010 exerts lateral force on the main delivery channel 4110 to pinch the channel 4110 shut, as discussed above. Moreover, the tissue flap formed by the blades may provide a second check valve that further reduces backflow of therapeutic agent 4010. The therapeutic agent 4010 may tend to flow up the secondary channel 4112 once the delivery device 2100 is extracted; thus, the therapeutic agent 4010 may seek to flow proximally until encountering the tissue flap at the corner between the secondary channel 4112 and the main channel 4110. Backflow force of the therapeutic agent 4010 at this corner may cause the flap to fold against the main channel 4110, thereby occluding the main channel 4110 and stopping backflow.

In some embodiments, multiple cuts in the tissue form multiple tissue flaps, and back pressure of the therapeutic agent 4010 pushes the flaps together after the agent 4010 is delivered, thereby preventing the agent 4010 from leaking.

It will be understood that the delivery devices according to the embodiments may be implanted into a patient with use of a delivery system. The delivery devices may be a part of the delivery system. The delivery system may be any known delivery system configured to advance and control the advancement of the delivery device to the treatment site. Such a delivery system may be manual, automatic, or have a combination of automatic and manual functionalities, for example utilizing computer controls initiated by a clinician. FIGS. 33 through 37 show an example of a delivery system 3310 that may be used with the delivery device 2100, as well as the delivery devices shown in FIGS. 1 through 32.

Figure 33:
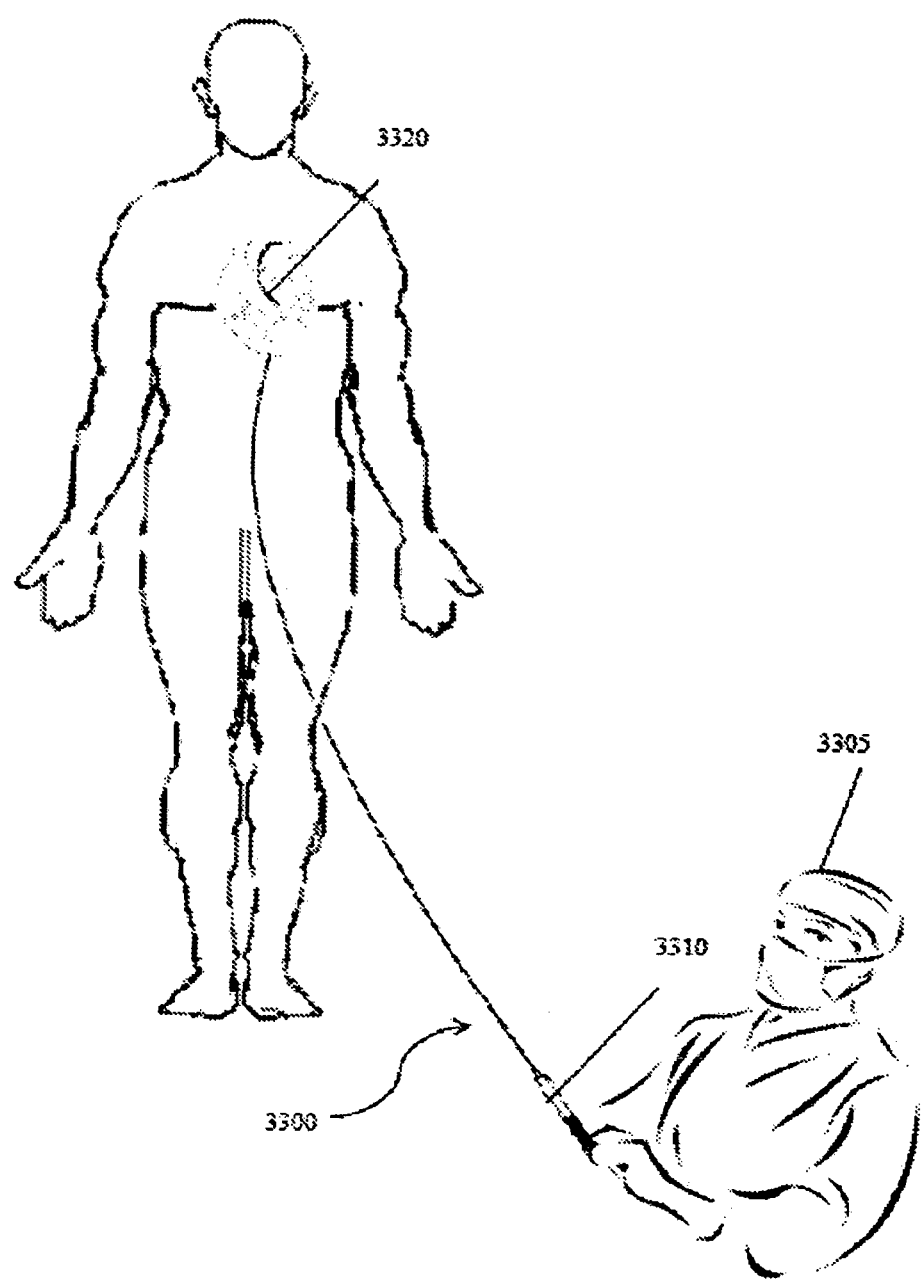
FIG. 33 shows a delivery system according to embodiments.
Figure 34:
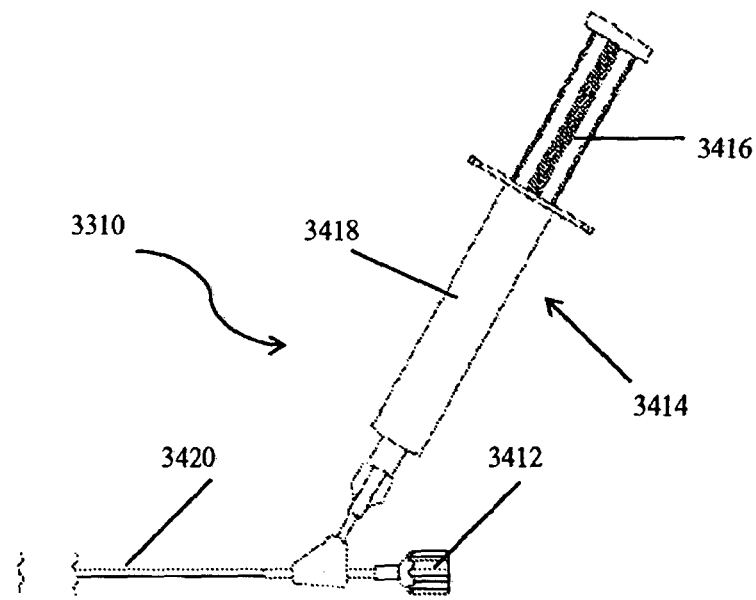
FIG. 34 shows a partial view of a delivery system.
Figure 35:
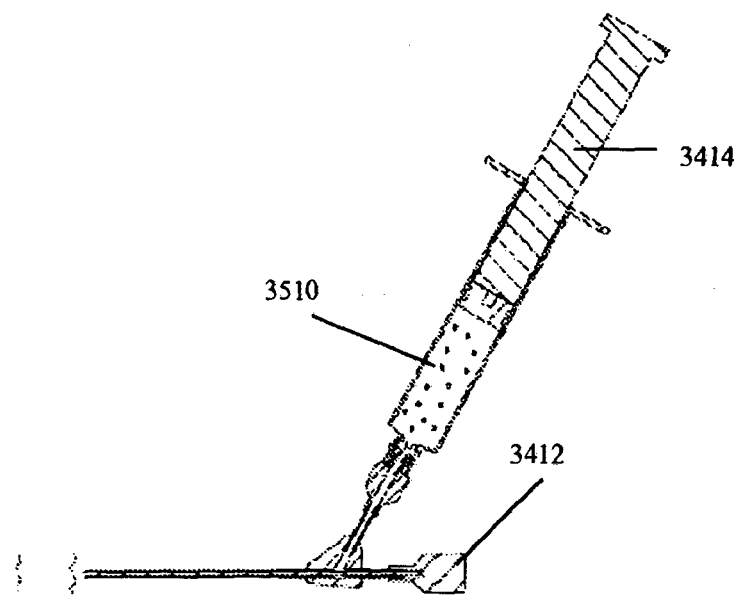
FIG. 35 shows a cross-sectional view of the delivery system of FIG. 34.

As shown in FIG. 33, the delivery systems and/or devices 3300 may be configured so that a clinician 3305 may percutaneously advance a delivery device to a treatment site 3320, for example, by using a micromanipulator 3310. In some embodiments, the delivery system 3300 may include a guide wire configured to advance the delivery device to the treatment site. It will be understood that the delivery systems are not limited to those shown in the figures and the delivery devices may be used with other delivery systems. It will also be understood that a clinician may use another delivery system to control the operation of the disclosed delivery devices.

FIGS. 34 through 37 show embodiments of the micromanipulator 3310. In some embodiments, the micromanipulator 3310 may include a positioning device 3412 and an injection device 3414. In some embodiments, the positioning device 3412 and the injection device 3414 may be fluidly connected to a delivery device according to embodiments by conduit 3420. The conduit 3420 may be, for example, any known medical tubing.

Figure 36:
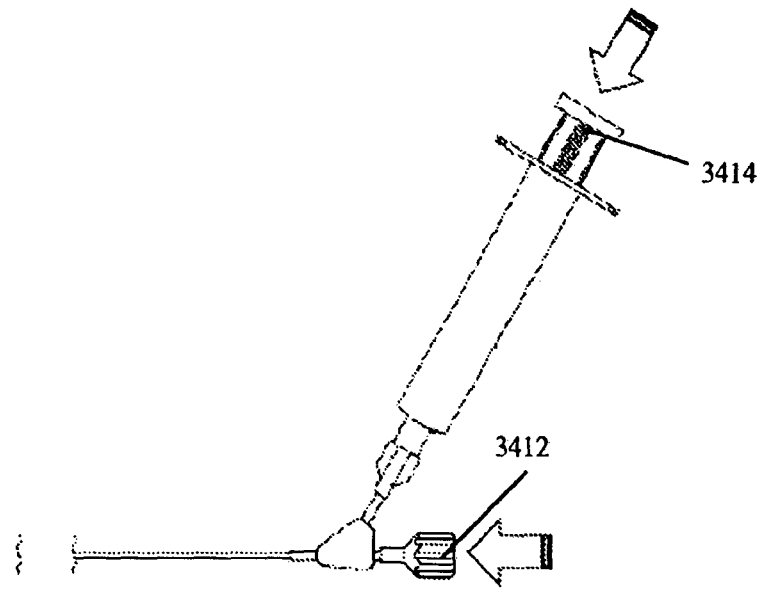
FIG. 36 shows a different state of operation of the delivery system of FIG. 34.

In some embodiments, the positioning device 3412 may be configured to advance the delivery device according to embodiments to the treatment site and/or position the delivery device at the treatment site. For example, the positioning device 3412 may be configured to rotate the elongate member with respect to the sheath when the delivery device has been advanced to the delivery device. The positioning device 3412 may be configured to manipulate a guide wire. In some embodiments, the positioning device 3412 may be a rotatable nob. As shown in FIG. 36, after a delivery device 3412 has been advanced to the treatment site, the positioning device 3412 may be rotated to move the elongate member with respect to the sheath. For example, by rotating the positioning device 3412, the elongate member may be moved forward toward the first end of the sheath so that the penetrating member is in the protruded position, for example, as shown in FIG. 38.

Figure 37:
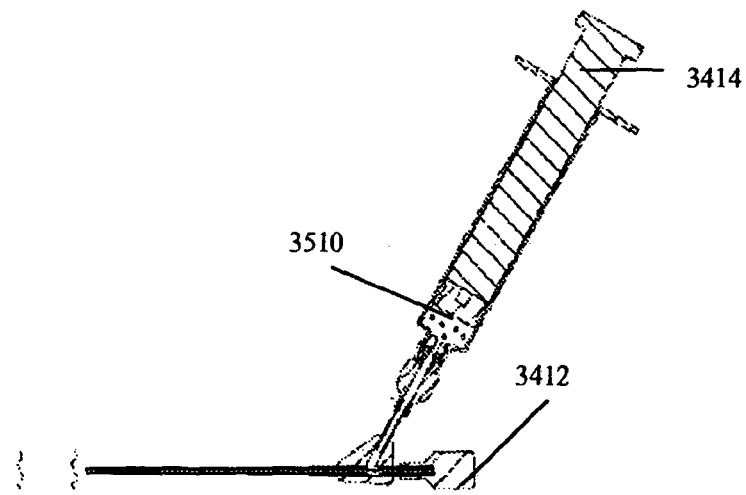
FIG. 37 shows a cross-sectional view of the delivery system of FIG. 36.

In some embodiments, the injection device 3414 may include a plunger 3414 and a tube 3418. The tube 3418 may be configured to hold a therapeutic agent 3510. As shown in FIGS. 36 and 37, the injection device 3414 may be configured to carry the agent 3510 to a delivery device according to embodiments after the elongate member has been positioned in an extended position with respect to the sheath. For example, FIG. 39 shows the agent being delivered by a delivery device to a treatment site.

In some embodiments, the delivery device may be sterilized. In some embodiments, one, some, or all parts of the delivery device may be reused. In further embodiments, one, some, or all parts of the delivery may be disposable. In further embodiments, the delivery device may be a single, use device.

In some embodiments, the delivery device may be part of a kit. In some embodiments, the kit may include the sheath and/or the elongate member. In some embodiments, the kit may include a guide wire.

In some embodiments, the delivery device may be preloaded with the therapeutic agent. In other embodiments, the agent may be loaded into the delivery device via a cartridge.

While the disclosure has been described in detail with reference to exemplary embodiments, those skilled in the art will appreciate that various modifications and substitutions can be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:
1. A device for delivering an agent to a treatment site, comprising:
   a sheath having a first end, a second end, and a length between the first end and the second end, the sheath including an outer diameter and an inner channel between the first end and the second end, the sheath including at least one penetrating member configured to form a channel at the treatment site, the penetrating member being configured to be movable between a first position and a second position, the first position corresponding to when the penetrating member is substantially aligned with the outer diameter, and the second position corresponding to when the penetrating member protrudes from the outer diameter at an angle towards one of the first end and the second end; and an elongate member having a first end, a second end, and a length between the first end and the second end, the elongate member being configured to move relative to the sheath;

wherein the elongate member is configured to control the movement of the penetrating member with respect to the sheath.

2. The device of claim 1, wherein the device is configured to deliver the agent when the penetrating member is in the second position.

3. The device of claim 1, wherein the channel includes at least one of a delivery channel and/or pressure channel.

4. The device of claim 1, wherein the elongate member includes a plurality of diameters, the diameters being configured to control the movement of the penetrating member.

5. The device of claim 1, wherein the sheath further includes a depressible section, the depressible section being configured to move between an aligned position and a depressed position, the aligned position corresponding to when the depressible section is substantially aligned with the outer diameter and the depressed position corresponding to when the depressible section is depressed into the inner channel of the sheath.

6. The device of claim 5, wherein:
the penetrating member and the depressible section being configured so that the position of the penetrating member depends on the position of the depressible section; and
the elongate member is configured to control the movement of the depressible section.

7. The device of claim 6, wherein the elongate member includes at least one tapered surface configured to cause the depressible section to move to the depressed position when adjacent to a portion of the depressible section.

8. The device of claim 6, wherein the sheath includes at least one opening configured to deliver the agent to the treatment site.

9. The device of claim 8, wherein:
the sheath includes two opposing penetrating members; and
the sheath includes two opposing openings, each of the penetrating members being configured to be disposed within one of the openings when in the first position, and the penetrating members being configured to expose each of the openings when in the second position.

10. The device of claim 9, wherein the delivery device is configured to deliver the agent through the openings when the penetrating members are in the second position.

11. The device of claim 8, wherein:
the penetrating member has a length and an inner channel that extends along the length;
the opening is disposed at one end of the channel; and
the delivery device is configured to deliver the agent through the opening when the penetrating member is in the second position.

12. A device for delivering an agent to a treatment site, comprising:
a sheath having a first end, a second end, and a length between the first end and the second end, the sheath having an outer diameter, the sheath including a section that is configured to reversibly depress from the outer diameter, the sheath including at least one penetrating member configured to be movable between an aligned position and a protruded position with respect to the length disposed at the section; and an elongate member having a first end, a second end, and a length between the first end and the second end, the elongate member being configured to move relative to the sheath;

wherein the aligned position corresponds to when the penetrating member is parallel with the outer diameter and the protruded position corresponds to when the penetrating member protrudes from the outer diameter into the treatment site; and wherein the elongate member includes a plurality of sections, at least one of the sections of the elongate member being configured to control the position of at least the penetrating member based on position of the elongate member with respect to the sheath.

13. The device of claim 12, wherein the elongate member includes at least a first section, a second section, and a third section, and the sections having different diameters.

14. The device of claim 12, wherein the section of the sheath is configured to be depressed when one of the sections is adjacent to a portion of the section of the sheath.

15. The device of claim 13, wherein the penetrating member is configured to protrude from the outer diameter when the section of the sheath is depressed from the outer diameter.

16. The device of claim 12, wherein the penetrating member has an elongated shape and a length, and a channel along the length.

17. The device of claim 12, wherein:
the sheath includes an opening that corresponds to each penetrating member;
the penetrating member being configured to be disposed within the opening when in the aligned position; and
the penetrating member being configured to expose the opening when in the protruded position.

18. The device of claim 17, wherein the elongate member is configured to control a size of each opening.

19. The device of claim 12, wherein the sheath includes two opposing penetrating members and openings, the openings being of different sizes.

* * * * *